US007820602B2

(12) United States Patent
Ravichandran et al.

(10) Patent No.: US 7,820,602 B2
(45) Date of Patent: Oct. 26, 2010

(54) AMINE TUNGSTATES AND LUBRICANT COMPOSITIONS

(75) Inventors: Ramanathan Ravichandran, Suffern, NY (US); Farouk Abi-Karam, Wilton, CT (US); Alena Yermolenka, Norwalk, CT (US); Michel Hourani, Brookfield, CT (US); Ingo Roehrs, Sandy Hook, CT (US)

(73) Assignee: King Industries, Inc., Norwalk, CT (US)

( * ) Notice: Subject to any disclaimer, the term of this patent is extended or adjusted under 35 U.S.C. 154(b) by 528 days.

(21) Appl. No.: 11/457,144

(22) Filed: Jul. 12, 2006

(65) Prior Publication Data

US 2007/0042917 A1  Feb. 22, 2007

Related U.S. Application Data

(60) Provisional application No. 60/698,750, filed on Jul. 12, 2005.

(51) Int. Cl.
*C10M 125/20* (2006.01)
*C10M 133/12* (2006.01)
*C10M 133/58* (2006.01)
*C10M 135/36* (2006.01)

(52) U.S. Cl. .............. 508/364; 508/167; 508/563; 508/251

(58) Field of Classification Search .............. 508/165, 508/170, 362, 364, 167, 563, 251
See application file for complete search history.

(56) References Cited

U.S. PATENT DOCUMENTS

| | | | |
|---|---|---|---|
| 2,492,314 A | 12/1949 | Olin et al. | |
| 2,744,069 A | 5/1956 | Loon | |
| 3,087,436 A | 4/1963 | Dettlof et al. | |
| 3,087,936 A | 4/1963 | Le Suer | |
| 3,172,892 A | 3/1965 | Le Suer et al. | |
| 3,215,707 A | 11/1965 | Rense | |
| 3,231,587 A | 1/1966 | Rense | |
| 3,254,025 A | 5/1966 | Le Suer | |
| 3,272,746 A | 9/1966 | Le Suer et al. | |
| 3,290,245 A * | 12/1966 | Scotchford et al. | 508/362 |
| 3,356,702 A | 12/1967 | Farmer et al. | |
| 3,361,673 A | 1/1968 | Stuart et al. | |
| 3,381,022 A | 4/1968 | Le Suer | |
| 3,382,172 A | 5/1968 | Lowe | |
| 3,401,118 A | 9/1968 | Benoit, Jr. | |
| 3,458,470 A * | 7/1969 | Edgar | 524/406 |
| 3,502,677 A | 3/1970 | Le Suer | |
| 3,567,638 A | 3/1971 | Braid | |
| 3,595,791 A | 7/1971 | Cohen | |
| 3,649,229 A | 3/1972 | Otto | |
| 3,652,616 A * | 3/1972 | Watson et al. | 556/62 |
| 3,664,954 A * | 5/1972 | Chiola et al. | 508/362 |
| 3,704,315 A | 11/1972 | Strang | |
| 3,798,165 A | 3/1974 | Piasek et al. | |
| 3,912,764 A | 10/1975 | Palmer, Jr. | |
| 4,098,705 A | 7/1978 | Sakurai et al. | |
| 4,102,798 A | 7/1978 | Ryer et al. | |
| 4,110,349 A | 8/1978 | Cohen | |
| 4,113,639 A | 9/1978 | Lonstrup et al. | |
| 4,116,876 A | 9/1978 | Brois et al. | |
| 4,215,067 A | 7/1980 | Brannen et al. | |
| 4,234,435 A | 11/1980 | Meinhardt et al. | |
| 4,298,485 A | 11/1981 | Powers et al. | |
| 4,529,526 A | 7/1985 | Inoue et al. | |
| 4,686,054 A | 8/1987 | Wisotsky et al. | |
| 4,761,482 A | 8/1988 | Karol | |
| 4,792,410 A | 12/1988 | Schwind et al. | |
| 4,816,303 A * | 3/1989 | Kroenke et al. | 428/333 |
| 4,846,983 A | 7/1989 | Ward, Jr. | |
| 4,857,214 A | 8/1989 | Papay et al. | |
| 4,880,437 A | 11/1989 | Karol | |
| 5,110,488 A | 5/1992 | Tipton et al. | |
| 5,366,648 A * | 11/1994 | Salomon et al. | 508/251 |
| 5,378,787 A | 1/1995 | Vrckovnik et al. | |
| 5,415,792 A * | 5/1995 | Campbell | 508/459 |
| 5,498,809 A * | 3/1996 | Emert et al. | 585/13 |
| 5,614,124 A | 3/1997 | Esche, Jr. et al. | |
| 5,627,146 A | 5/1997 | Tanaka et al. | |
| 5,824,627 A | 10/1998 | McConnachie et al. | |
| 5,906,969 A * | 5/1999 | Fyfe | 508/364 |
| 6,211,123 B1 | 4/2001 | Brown et al. | |
| 7,335,625 B2 * | 2/2008 | Tynik | 508/362 |
| 2003/0027731 A1 * | 2/2003 | Kawamura et al. | 508/552 |

(Continued)

FOREIGN PATENT DOCUMENTS

EP  0 024 146  2/1981

(Continued)

*Primary Examiner*—Glenn Caldarola
*Assistant Examiner*—Jim Goloboy
(74) *Attorney, Agent, or Firm*—Jones Day

(57) ABSTRACT

This invention relates to lubricating oil additives, and to lubricating oil compositions, their method of preparation, and use. More specifically, this invention relates to several novel lubricating oil additives and compositions which contain a tungsten compound and an antioxidant, namely aminic antioxidants such as a secondary diarylamine or an alkylated phenothiazine. The use of the tungsten compound with the secondary diarylamine and/or the alkylated phenothiazine provides improved oxidation and deposit control to lubricating oil compositions. The lubricating oil compositions of this invention are particularly useful as crankcase and transmission lubricants, gear oils and other high performance lubricant applications.

25 Claims, No Drawings

U.S. PATENT DOCUMENTS

| | | | |
|---|---|---|---|
| 2003/0224950 A1* | 12/2003 | Esche et al. | 508/251 |
| 2004/0214731 A1* | 10/2004 | Tynik | 508/362 |
| 2007/0203032 A1* | 8/2007 | Tynik et al. | 508/246 |
| 2007/0203033 A1* | 8/2007 | Tynik et al. | 508/362 |

FOREIGN PATENT DOCUMENTS

| | | |
|---|---|---|
| GB | 984 409 | 2/1965 |
| GB | 1 440 219 | 6/1976 |
| WO | WO 99/66011 A2 | 12/1999 |
| WO | WO 2004/043910 | 5/2004 |

* cited by examiner

AMINE TUNGSTATES AND LUBRICANT COMPOSITIONS

This application claims the benefit of priority to U.S. Provisional Application 60/698,750, filed on Jul. 12, 2005. The contents of this U.S. Provisional Application are hereby incorporated by reference in its entirety.

FIELD OF THE INVENTION

This invention relates to lubricating oil additives, and to lubricating oil compositions, their method of preparation, and use. More specifically, this invention relates to several novel lubricating oil additives and compositions which contain a tungsten compound and an antioxidant, namely aminic antioxidants such as a secondary diarylamine or an alkylated phenothiazine. The use of the tungsten compound with the secondary diarylamine and/or the alkylated phenothiazine provides improved oxidation and deposit control to lubricating oil compositions. The lubricating oil compositions of this invention are particularly useful as crankcase and transmission lubricants, gear oils and other high performance lubricant applications.

BACKGROUND OF THE INVENTION

Lubricating oils as used in, for example, the internal combustion engines of automobiles or trucks are subjected to a demanding environment during use. This environment results in the oxidation of the oil catalyzed by the presence of impurities in the oil, such as iron compounds, and is also promoted by the elevated temperatures experienced by the oil during use. This catalyzed oxidation of the oil not only contributes to the formation of corrosive oxidation products and sludge in the oil but can also cause the viscosity of the oil to increase or even cause the oil to solidify. This oxidation of lubricating oils during use is usually controlled to some extent by the use of antioxidant additives which may extend the useful life of the oil, for example, by reducing or preventing unacceptable viscosity increases.

Aminic antioxidants are antioxidants that contain one or more nitrogen atoms, such as alkylated diphenyl amines and phenothiazines. Phenolic antioxidants contain one or more sterically hindered phenol functionalities, and can be either used alone or in synergistic combinations with alkylated aminic antioxidants. The synthesis and uses of phenolic antioxidants, phenothiazines and aromatic amines have been reported. Phenothiazine antioxidants have been used as a stand alone additive, chemically modified or grafted onto the backbone of polymers.

There is, however, a continuing need for new antioxidants and antioxidant systems which offer improved performance and which are effective at low levels. There are a number of factors which have contributed to this continuing need. One such factor is that in recent years internal combustion engines are often operated at even higher temperatures, which tend to increase the rate of oxidation and shorten the useful life of the oil. In addition, there is a strong desire to use cheaper base stocks for lubricating oil compositions which have inferior resistance to oxidation and require more efficient and effective antioxidants. There is also a need for lubricating oils to have a longer in service life span to support the longer service intervals for motor vehicles. There is also a desire to find antioxidants and antioxidant systems which meet the above requirements and at the same time are not detrimental to other aspects of motor vehicle performance. In this respect there is a desire for antioxidants which do not contribute to the phosphorus content of motor vehicle exhausts, as phosphorus is detrimental to the performance of catalyst based exhaust purification systems. The trend to reduce phosphorus levels in the final formulation has led to use of lower levels of zinc dialkyldithiophosphates, (ZDDP). This has led to an overall reduction in the levels of antioxidants used in the final formulation because ZDDP also serves as an antioxidant, in addition to an extreme-pressure/antiwear additive. The trend to reduce the total levels of sulfur in lubricants will also lead to lower use levels of sulfur containing multifunctional antioxidant extreme-pressure additives such as sulfurized olefins, and other sulfur containing detergents. In addition some antioxidants, such as for example diphenylamines, cannot be used at relatively high concentrations as this may result in sedimentation or deposits in hot engine areas such as the diesel ring areas in diesel engines. The invention is concerned with the problem of providing an improved antioxidant for use in lubricating oils.

SUMMARY OF THE INVENTION

This invention relates to new tungsten containing lubricating oil additives, compositions, their method of preparation, and use. More specifically, this invention relates to lubricating oil compositions which contain a tungsten compound and an aminic antioxidant such as alkylated diphenyl amines and/or alkylated phenothiazines. In addition the composition may additionally include a sulfur-containing additive such as sulfurized olefins, sulfurized vegetable oils, sulfurized animal fats and oils, sulfurized fatty acids, sulfurized synthetic esters, sulfurized acrylates and sulfurized methacrylates, and sulfurized succinic acid derivatives, thiadiazole, dithiocarbamate, dithiophosphate and mixtures thereof. The use of both the tungsten containing additive and the alkylated secondary diarylamine, and alternatively further with phenothiazine, provides improved oxidation and deposit control to lubricating oil compositions. The lubricating oil compositions of this invention are particularly useful as crankcase and transmission lubricants, gear oils and other high performance lubricant applications.

The antioxidant additive compositions of this invention result in low levels of deposits and display improved corrosion inhibition and friction properties.

This invention provides compositions comprising certain tungsten containing compounds and antioxidants, namely certain aromatic amines, either alone or in combination with phenolic antioxidants, that provide a highly effective regenerative antioxidant system for use in lubricating oils, especially in lubricating oils for gasoline and diesel engines. Lubricating oils as used in the internal combustion engines and transmissions of automobiles or trucks, gear oils and other high temperature lubricant applications are subjected to a demanding environment during use. This environment results in the oxidation of oil which is catalyzed by the presence of impurities in the oil (such as iron compounds) and promoted by the elevated temperatures of the oil during use.

DETAILED DESCRIPTION OF THE INVENTION

This invention provides compositions containing various amine tungstate compounds and various amine additives which display synergistically enhanced friction reducing properties compared to previously reported amine tungstate-based compositions that include sulfur or phosphorus compounds and additional metallic additives.

It has been found that the combination of (1) an oil soluble or dispersible tungsten compound and (2) a secondary diarylamine, such as an alkylated diphenylamine, either alone or in combination with also preferably an alkylated, phenothiazine, is highly effective at controlling crankcase lubricant oxidation and deposit formation. Examples of the types of compounds that may be used in this invention are described in the following. The tungsten compound may be used between 20 and 4000 ppm, preferably between 20 to 1000 ppm, based on the amount of tungsten delivered to the finished lubricating oil. Alkylated phenothiazines, secondary diarylamines, and other suitable aminic antioxidants may be used at concentrations ranging from 0.05 to 2.5 wt. % in the finished lubricant, preferably between 0.1 to 1.0 wt. %. In some embodiments of the invention, an oil soluble or dispersible molybdenum compound may be substituted for the tungsten compound. In addition to the antioxidants of this invention, the lubricating composition may also contain dispersants, detergents, antiwear additives including for example ZDDP, ashless dithiophosphates, ashless phosphorothioates and thiophosphates, ashless dithiocarbamates, additional antioxidants if required, friction modifiers, corrosion inhibitors, anti-foaming additives, pour point depressants and viscosity index improvers. The lubricant may be prepared from any paraffinic, naphthenic, aromatic, or synthetic base oil, or mixtures thereof. In an embodiment, the lubricant may contain between 250 and 1000 ppm of phosphorus derived from ZDDP and between 500 and 3000 ppm of calcium from calcium containing sulfonate detergents or calcium containing phenate detergents. In this manner, both crankcase and automatic transmission fluid (ATF) lubricants, gear oils and other high temperature lubricants are readily prepared.

Thus, one embodiment of the present invention provides crankcase and transmission fluid lubricants, gear oils and other high temperature industrial lubricants and additive package concentrates, which contain very low levels of phosphorus. More preferred are lubricant compositions containing zero or essentially zero phosphorus. By "essentially zero phosphorus" herein is meant phosphorus levels of less than or equal to about 100 ppm.

In another embodiment, the lubricant does not contain ZDDP, but may contain other sources of phosphorus, including ashless dithiophosphates, I. Tungsten Compounds of the Current Invention and their Preparation 1.0 Sulfur- and Phosphorus-Free Organotungsten Compounds Sulfur- and phosphorus-free organotungsten compounds that are a component of the present invention may be prepared by reacting a sulfur and phosphorus-free tungsten source with an organic compound containing an amino group. Examples of sulfur- and phosphorus-free tungsten sources include tungstic acid, tungsten trioxide, ammonium ortho tungstate, ammonium para tungstate, ammonium meta tungstate, sodium tungstate and potassium tungstate. The amino groups may be monoamines, diamines, or polyamines, containing primary, secondary or tertiary amine functionalities. The primary amine structure may be

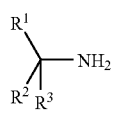

which $R^1$, $R^2$ and $R^3$ are independently hydrogen, $C_1$-$C_{25}$ alkyl, $C_2$-$C_{25}$ alkyl interrupted by oxygen or sulfur; $C_2$-$C_{24}$ alkenyl, $C_4$-$C_{15}$ cycloalkyl which is unsubstituted or substituted by $C_1$-$C_4$ allyl and/or carboxyl; $C_5$-$C_{15}$ cycloalkenyl which is unsubstituted or substituted by $C_1$-$C_4$ alkyl and/or carboxyl; $C_{13}$-$C_{26}$ polycycloalkyl, $C_7$-$C_9$ phenylalkyl which is unsubstituted or substituted on the phenyl ring by $C_1$-$C_4$ alkyl; —COR6, a 5- or 6-membered heterocyclic ring which is unsubstituted or substituted by $C_1$-$C_4$ alkyl, $C_1$-$C_4$ alkoxy, halogen or carboxyl; a 5- or 6-membered heterocyclic ring which is benzo-fused and is unsubstituted or substituted by $C_1$-$C_4$ alkyl, $C_1$-$C_4$ alkoxy, halogen or carboxyl.

For example, the secondary amine is of the following structure

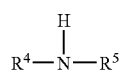

wherein $R^4$ and $R^5$ are independently hydrogen, linear, branched, saturated or unsaturated alkyl of 1 to 40 carbon atoms, cycloalkyl of 5 to 40 carbon atoms, aryl of 6 to 40 carbon atoms, aralkyl of 7 to 9 carbon atoms, where the aralkyl may be substituted by alkyl of 1 to 36 carbon atoms.

The tertiary amine is preferably represented by general formula

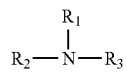

wherein $R_1$, $R_2$, and $R_3$ are independently each a $C_1$ to $C_{36}$ residue that may optionally contain at least one —O—, —S—, —SO—, —CO_2—, —CO—, or —CON— moiety, cycloalkyl of 5 to 12 carbon atoms, aralkyl of 7 to 9 carbon atoms, where the aralkyl may be substituted by alkyl of 1 to 36 carbon atoms.

Specific examples of the amine tungstates are those derived from Primene JM-T, tert-octadecylamine, tert-eicosylamine, 1-methyl-1-ethyl octadecyl amine, 1,1-dimethyl octadecylamine, 1-methyl-1-butyl hexadecylamine, 1-triacontylamine, oleyl amine, lauryl amine, and tall oil amine.

Polyamines are preferably represented by general formula

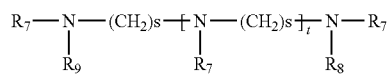

wherein $R_7$, $R_8$ and $R_9$ are each independently hydrogen; $C_1$ to $C_{25}$ straight or branched chain alkyl radicals; $C_1$ to $C_{12}$ alkoxy-($C_6$ alkylene) radicals; $C_2$ to $C_{12}$ alkylamino-$C_2$ to $C_6$ alkylene) radicals; each s can be the same or a different number of from 1 to 6, preferably 2 to 4; and t is a number from 0 to 10, preferably 2 to 7. At least one of $R_7$, $R_8$ and $R_9$ must be hydrogen.

Suitable amines include: 1,2-diaminoethane; 1,3-diaminopropane; 1,4-diaminobutane; 1,6-diaminohexane; polyethylene amines such as diethylene triamine; triethylene tetramine; tetraethylene pentamine; polypropylene amines such as 1,2-propylene diamine; di-(1,2-propylene)triamine; di(1,3-propylene)-triamine; N,N-dimethyl-1,3-diaminopropane; N,N-di-(2-aminoethyl)ethylene diamine; N,N-di(2-hydroxyethyl)-1,3-propylene diamine; 3-dodecyloxypropylamine; N-dodecyl-1,3-propane diamine; tris hydroxymethylaminomethane (THAM); diisopropanol amine; diethanol amine; triethanol amine; amino morpholines such as N-(3-aminopropyl)morpholine; etc.

In order to improve solubility of the organotungsten product in base oils and finished oils, it is useful for the mono-substituted diamine to have a high hydrocarbon character. For example, the diamine can be represented by the following general structure:

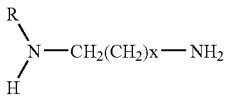

where x is 1 or 2, and R is a hydrocarbon-containing group containing a minimum of about 6 carbon atoms, and up to 24 carbon atoms. R can be aliphatic or aromatic. R, in addition to the minimum of about 6 carbon atoms, may also contain oxygen, but preferably R does not include sulfur or additional nitrogen. It is preferred that R contains a minimum of 10 carbon atoms in order to further improve the organotungsten product solubility in base oil. The most preferred R contains oxygen in addition to the carbons, such as where R is an alkyloxyalkylene group. Where R represents an alkyloxyalkylene group, R can be represented by the structure —$X_1$—O—$X_2$, where $X_1$ is an alkylene of 2, 3 or 4 carbons and preferably is propylene or ethylene, and $X_2$ is an alkyl moiety having 3 to 30 carbon atoms, more preferably an alkyl moiety having 7 to 20 carbon atoms, and where $X_2$ can be a straight or branched, saturated or partially unsaturated hydrocarbon chain.

Examples of some mono-substituted diamines that may be used include phenylaminopropylamine, hexylaminopropylamine, benzylaminopropylamine, octylaminopropylamine, octylaminoethylamine, dodecylaminopropylamine, dodecylaminoethylamine, hexadecylaminopropylamine, hexadecylaminoethylamine, octadecylaminopropylamine, octadecylaminoethylamine, isopropyloxypropyl-1,3-diaminopropane, octyloxypropyl-1,3-diaminopropane, decyloxypropyl-1,3-diaminopropane, isodecyloxypropyl-1,3-diaminopropane, dodecyloxypropyl-1,3-diaminopropane, tetradecyloxypropyl-1,3-diaminopropane, isodecyloxypropyl-1,3-diaminopropane, isododecyloxypropyl-1,3-diaminopropane, isotridecyloxypropyl-1,3-di a-minopropane. Mono-substituted diamines derived from fatty acids may also be used. Examples include N-coco alkyl-1,3-propanediamine (Duomeen C), N-tallow alkyl-1,3-propanediamine (Duomeen T), and N-oleyl-1,3-propanediamine (Duomeen OL), all obtained from Akzo Nobel.

Other useful amine compounds include alicyclic diamines such as 1,4-di-(aminomethyl)cyclohexane, and heterocyclic nitrogen compounds such as imidazolines, and N-aminoalkyl piperazines of the general formula:

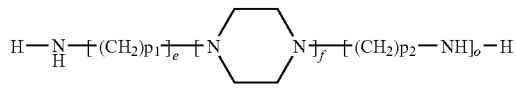

wherein $p_1$ and $p_2$ are the same or different and each is an integer from 1 to 4, and e, f and o are the same or different and each is an integer from 1 to 3.

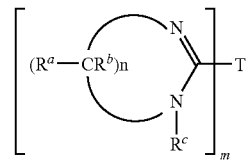

in which n=2 or 3, m=1 or 2, $R^a$, $R^b$ and $R^c$ are identical or different, and represent hydrogen, alkyl, or substituted alkyl, hydroxyalkyl, aryl, aralkyl, cycloalkyl, heterocyclics, ether, thioether, halogen, —$N(R)_2$, polyethylene polyamines, nitro groups, keto groups, ester groups, or carbonamide groups, alkyl substituted with the various functional groups described above, and T represents alkyl, alkylene, aryl, aralkyl, cycloalkyl or heterocyclic radical, substituted if desired with halogen, nitro groups, alkyl groups, alkoxy groups or amino groups, and, when m=1, T represents hydrogen. Salts of the above structures include carboxylic including aliphatic, aromatic and poly carboxylic, carbonic, sulfonic and phosphoric acid salts.

$R^a$, $R^b$, $R^c$ are independently hydrogen, alkyl, alkenyl, or alkoxy of 1 to 36 carbons, cycloalkyl of 6 to 32 carbons, alkylamino of 1 to 36 carbon atoms, cycloalkyl of 5 to 12 carbon atoms, phenyl, hydroxyalkyl, or hydroxycycloalkyl of 1 to 20 carbon atoms, methoxyalkyl of 1 to 20 carbon atoms, aralkyl of 7 to 9 carbon atoms, where the aryl group of the aralkyl is further substituted by alkyl of 1 to 36 carbon atoms. When m=2, T is alkylene of 1 to 12 carbons or arylene of 6 to 10 carbons, or a plurality of radicals being able to be joined, containing hetero atoms also by hetero atoms such as O, N or S, if desired.

Preferred imidazoline structures are where R is a long chain alkyl up to 18 carbon atoms, m=1 and $R^c$ is one of 2-hydroxyethyl, or 2-aminoethyl or 2-amido ethyl substituents.

Examples of such amines include 2-pentadecyl imidazoline, aminoethyl oleyl imidazoline and N-(2-aminoethyl)piperazine.

2.0 Sulfur-Containing Organotungsten Compounds

The sulfur-containing organotungsten compounds of the invention may be prepared by a variety of methods. One method involves reacting a sulfur and phosphorus-free tungsten source with an amino group and one or more sulfur sources. Non-limiting examples of sulfur sources include carbon disulfide, hydrogen sulfide, sodium sulfide and elemental sulfur. Alternatively, the sulfur-containing tungsten compounds may be prepared by the reaction of a sulfur-free tungsten source with an amino group or thiuram group and optionally a second sulfur source. Examples of sulfur- and phosphorus-free tungsten sources include tungstic acid, tungsten trioxide, ammonium ortho tungstate, ammonium meta tungstate, ammonium paratungstate, sodium tungstate, potassium tungstate and tungsten halides. The amino groups may be monoamines, diamines, or polyamines. As an example, the reaction of tungsten trioxide with a secondary amine and carbon disulfide produces tungsten dithiocarbamates.

An alternate approach includes the reaction of sulfur- and phosphorus-free tungsten sources including tungstic acid, tungsten trioxide, ammonium ortho tungstate, ammonium meta tungstate, ammonium paratungstate, sodium tungstate, and potassium tungstate with a sulfurated amine precursor.

Examples of sulfur containing organotungsten compounds appearing in patents and patent applications include the following all of which are hereby incorporation by reference in their entirety:

Compounds prepared by the reaction of divalent metal tungstates with dithiocarbamates in an alkaline sodium sulfide and/or sodium hydrogen sulfide solution as described in WO 2004/043910 A2.

Compounds prepared by the reaction of a primary amine with a $CS_2$ or COS, and subsequent reaction of the dithiocarbamic acid produced with a tungsten containing compound, as described in U.S. Pat. No. 4,846,983.

Sulfurized oxymetalorganophosphorodithioates, and sulfurized oxymetal dithiocarbamates as described in U.S. Pat. No. 4,529,526 wherein the metal is tungsten.

Tungsten dithiocarbamates are illustrated with the following structure,

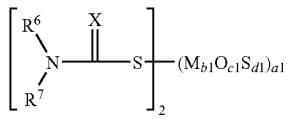

where $R^6$ and $R^7$ are independently the same or different and are selected from H and $C_1$ to $C_{30}$ and are an alkyl group, a cycloalkyl group, an aryl group or an alkaryl group, with the proviso that at least one of $R^6$ or $R^7$ is H for at least one of the thiocarbamate groups, and at least one of $R^6$ or $R^7$ is hydrocarbyl for each of the thiocarbamate groups, M is W, X is O or S, $b_1$ is at least 1, $a_1$ is at least 1 depending on the oxidation state of M, $c_1$ is at least 1 depending on the oxidation state of M and $d_1$ is 0 or at least 1 depending on the oxidation state of M. Generally, $a_1$ and $b_1$ will range from 1 to about 5, $c_1$ will range from 1 to about 6 and $d_1$ will be 0 or range from 2 to about 10. In a preferred embodiment, $a_1$ will be 1 or 2, $b_1$ will be 1 or 2, $c_1$ will be 1 or 2, and $d_1$ will be 0 or 2.

Sulfurized oxymetal organophosphorodithioates are illustrated with the following structure.

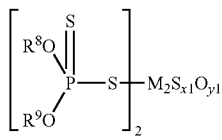

wherein M is tungsten, $R^8$ and $R^9$ may be the same or different, each of $R^8$ and $R^9$ contains from 1 to 30 carbon atoms and are selected from the group consisting of an alkyl group, a cycloalkyl group, an aryl group, and a alkylaryl group; and $x_1$ and $y_1$ are positive real numbers satisfying the equation: $x_1+y_1=4$.

3. Silicon Containing Organotungsten Compounds

The silicon containing organotungsten compound of this invention may be prepared by a variety of methods. One method involves reacting a sulfur and phosphorus-free tungsten source with an amino silane. Examples of sulfur- and phosphorus-free tungsten sources include tungstic acid, tungsten trioxide, ammonium ortho tungstate, ammonium meta tungstate, ammonium paratungstate, sodium tungstate and potassium tungstate.

Particularly useful are aminosilanes of the formula

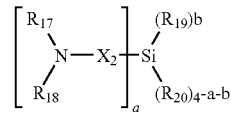

in which $R_{17}$ and $R_{18}$ are independently hydrogen, $C_1$-$C_{25}$ alkyl, 2-hydroxyethyl, $C_3$-$C_{25}$ alkyl which is interrupted by oxygen or sulfur; $C_2$-$C_{24}$ alkenyl or

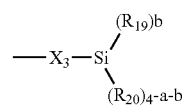

$R_{19}$ is $C_1$-$C_{25}$ alkyl, $C_2$-$C_{25}$ alkyl which is interrupted by oxygen or sulfur; hydroxyl, $C_1$-$C_{18}$ alkoxy or $C_2$-$C_{24}$ alkenyl, $R_{20}$ is hydroxyl, $C_1$-$C_{18}$ alkoxy or $C_2$-$C_{18}$ alkoxy which is interrupted by oxygen or sulfur; and, if a and b together are 1, three radicals $R_{20}$ together are $N(CH_2\ CH_2O—)_3$, $X_3$ is $C_1$-$C_{18}$ alkylene, $C_2$-$C_{20}$ alkylidene, $C_7$-$C_{20}$ phenylalkylidene, $C_5$-$C_8$ cycloalkylene, phenylene or naphthylene which is unsubstituted or substituted by $C_1$-$C_4$ alkyl; or is $C_4$-$C_{18}$ alkylene which is interrupted by oxygen, sulfur or

$R_{21}$ is hydrogen or $C_1$-$C_8$ alkyl with the proviso that two nitrogen atoms are not attached to the same carbon atom, a is 1 or 2, and b is 0, 1 or 2.

Examples of amino silanes useful in this invention include, aminopropyl triethoxysilane, aminopropyl trimethoxy silane, aminopropyl diethoxysilane, aminopropyl methyldimethoxysilane, aminoethyl aminopropyltrimethoxysilane, aminoethyl aminopropylmethyldimethoxysilane, aminoethyl aminopropylmethyldiethoxysilane, aminoethyl aminomethyltriethoxysilane, aminoethyl aminomethylmethyldiethoxysilane, diethylenetriaminopropyltrimethoxysilane, diethylenetriaminopropyltriethoxysilane, diethylenetriaminopropylmethyldimethoxysilane, diethylenetriaminopropylmethyldiethoxysilane, diethylenetriaminomethyldimethoxysilane, cyclohexylaminopropyltrimethoxysilane, cyclohexylaminopropyltriethoxysilane, cyclohexylaminopropylmethyldimethoxysilane, cyclohexylaminopropylmethyldiethoxysilane, cyclohexylaminomethyltriethoxysilane, cyclohexylaminomethylmethyldiethoxysilane, hexanediaminomethyltriethoxysilane, phenylaminomethyltrimethoxysilane, phenylaminopropyltrimethoxysilane, phenylaminopropyltriethoxysilane, phenylaminopropyl methyldimethoxysilane, phenylaminopropyl methyldiethoxysilane, phenylaminomethylmethyldimethoxysilane, phenylaminomethylmethyldiethoxysilane, phenylaminomethyltriethoxysilane, diethylaminomethyltriethoxysilane, diethylaminomethyltrimethoxysilane, diethylaminopropyltrimethoxysilane, diethylaminopropyl methyldimethoxysilane, diethylaminopropyl methyldiethoxysilane, dimethylaminopropyl methyldiethoxysilane, (diethylaminomethyl) methyldiethoxysilane, methylaminopropyltrimethoxysilane, bis((3-triethoxysilyl)propyl)amine, piperazinylpropylmethyldimethoxysilane, piperazinylpropylmethyldiethoxysilane, piperazinylmethylmethyldiethoxysilane, morpholinylpropyltrimethoxysilane, morpholinylpropyltriethoxysilane, morpholinylpropylmethyldimethoxysilane, morpholinylpropylmethyldiethoxysilane, morpholinylmethyltriethoxysilane, morpholinylmethylmethyldiethoxysilane, diaminomethylmethyldiethoxysilane, dimethyldiaminopropylmethyldiethoxysilane, dimethyldiaminomethylmethyldiethoxysilane, aminohexylaminomethyltrimethoxysilane, aminohexylaminopropyltrimethoxysilane, octanoylaminopropyltriethoxysilane, methylaminopropyltrimethoxysilane, methylaminopropylmethyldiethoxysilane, methylaminomethylmethyldiethoxysilane, ethylaminopropylmethyldiethoxysilane, ethyl aminomethylmethyldiethoxysilane.

Also useful are silicone amines commercially available from Siltech under the Silamine tradename. The structures mentioned in the U.S. Pat. No. 5,378,787, which is hereby incorporation by reference in its entirety, are also useful and are as follows:

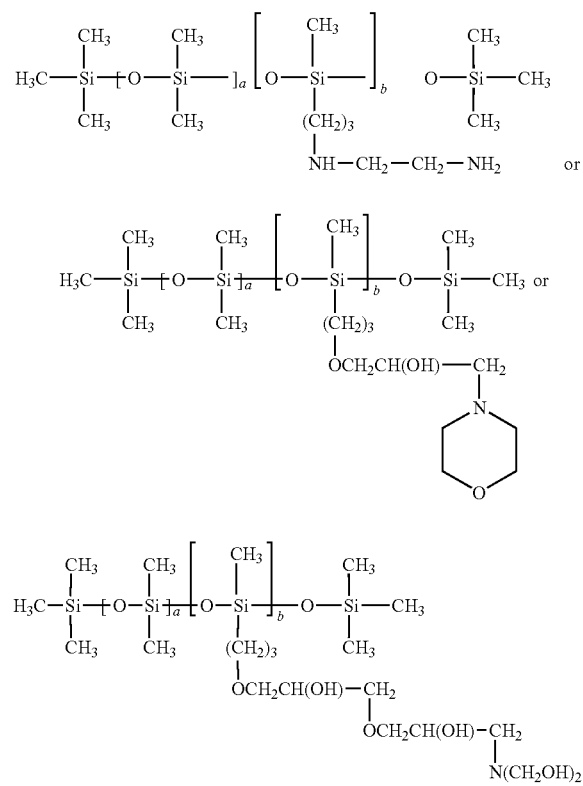

where a and b are integers ranging from 0 to 2000.

4.0 Organoamine Tungstates with Ethoxylated Amines

The organoamine tungstate compounds useful in the present invention may be prepared by a variety of methods. One method involves reacting a sulfur and phosphorus-free tungsten source with an ethoxylated amine. Examples of sulfur- and phosphorus-free tungsten sources include tungstic acid, tungsten trioxide, ammonium ortho tungstate, ammonium meta tungstate, ammonium paratungstate, sodium tungstate and potassium tungstate.

Particularly useful ethoxylated fatty amines are

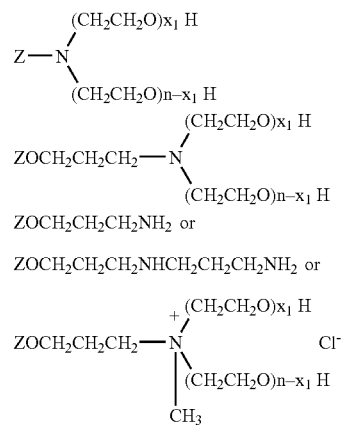

where Z is straight or branched chain alkyl of from about 8 to 26 carbon atoms, alkoxy alkyl of 4 to 22 carbon atoms, $n=2$ to about 50, and $x_1$=from about 1 to about 49.

Specific embodiments include, isopropyloxypropyl amine, isohexyloxypropyl amine, 2-ethylhexyloxypropyl amine, octyl/decyloxy propyl amine, isodecyloxypropyl amine, isododecyloxypropyl amine, dodecyl/tetradecyloxypropyl amine, isotridecyloxypropyl amine, tetradecyloxypropyl amine, linear alkoxypropyl amine, octadecyl/hexadecyloxypropyl amine, octyl/decyloxy propyl-1,3-diaminopropane, isodecyloxypropyl 1,3-diaminopropane, isododecyloxypropyl 1,3-diaminopropane, dodecyl/tetradecyloxypropyl 1,3-diaminopropane, isotridecyloxypropyl 1,3-diaminopropane, tetradecyloxypropyl 1,3-diaminopropane, bis-(2-hydroxyethyl)isodecyloxypropyl amine, bis-(2-hydroxyethyl)isotridecyloxypropyl amine, bis-(2-hydroxyethyl) linear alkoxypropyl amine, bis-(2-hydroxyethyl)soya amine, bis-(2-hydroxyethyl)tallow amine, poly(5)oxyethylene isodecyloxypropyl amine, poly(5)oxyethylene isotridecyloxypropyl amine, N-tallow-poly(3) oxyethlene-1,3-diaminopropane, isodecyloxypropyl bis-(2-hydroxyethyl)methyl ammonium chloride, isotridecyloxypropyl bis-(2-hydroxyethyl)methyl ammonium chloride, octadecyl bis-(2-hydroxyethyl)methyl ammonium chloride, isotridecyloxypropyl poly (5)oxyethylene methyl ammonium chloride, monosoya methyl ammonium chloride, tallow diamine diquaternary coco poly(15) oxyethylene methyl ammonium chloride and trimethyl stearyl ammonium chloride.

5. Organoamine Tungstates with Alkylated Phenothiazine

The organoamine tungstate compounds useful in the present invention may be prepared by a variety of methods. One method involves reacting a sulfur and phosphorus-free tungsten source with an alkylated phenothiazine. Examples of sulfur- and phosphorus-free tungsten sources include tungstic acid, tungsten trioxide, ammonium ortho tungstate, ammonium meta tungstate, ammonium paratungstate, sodium tungstate and potassium tungstate.

An alkylated phenothiazine suitable for this invention must be oil soluble or dispersible and correspond to the general formula below where the substituents $R_{11}$-$R_{14}$ could contain heteroatoms,

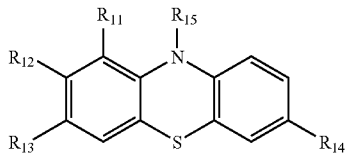

$R_{11}$ and $R_{12}$ are hydrogen or together can form a fused six-member aromatic ring.

One of $R_{13}$ and $R_{14}$ is hydrogen and the other is $C_2$-$C_{30}$ alkyl, cyclo-$C_5$-$C_{12}$ alkyl, —$C_2$-$C_4$ alkyl, α-$C_1$-$C_2$ alkylbenzyl or α,α-dimethylbenzyl; or both $R_{13}$ and $R_{14}$ are $C_2$-$C_{30}$ alkyl, cyclo-$C_5$-$C_{12}$ alkyl-$C_2$-$C_4$ alkyl, α-$C_1$-$C_2$ alkylbenzyl or α,α-dimethylbenzyl, if $R_{11}$ and $R_{12}$ hydrogen; or $R_{13}$ is hydrogen and $R_{14}$ is $C_2$-$C_{30}$ alkyl, cyclo-$C_5$-$C_{12}$ alkyl-$C_2$-$C_4$ alkyl, α-$C_1$-$C_2$ alkylbenzyl or α,α-dimethylbenzyl, if $R_{11}$ and $R_{12}$ together form a fused six-member aromatic ring.

$R_{15}$ is hydrogen, $C_1$-$C_{12}$ alkyl, benzyl, allyl, methallyl, phenyl or a group —$CH_2SR_4$, where $R_4$ is $C_4$-$C_{18}$ alkyl, —$CH_2CH_2COO(C_4$-$C_{18}$ alkyl), or an alkylene, aralkylene bridging two phenothiazine moieties.

Typical examples of alkylphenothiazine include but are not limited to monotetradecylphenothiazine, ditetradecylphenothiazine, monodecylphenothiazine, didecylphenothiazine monononylphenothiazine, dinonylphenothiazine, monooctylphenothiazine and dioctylphenothiazine.

6. Organoamine Tungstates with Alkylated Diarylamine

The organoamine tungstate compounds useful in the present invention may be prepared by a variety of methods. One method involves reacting a sulfur and phosphorus-free tungsten source with an alkylated diarylamine. Examples of sulfur- and phosphorus-free tungsten sources include tungstic acid, tungsten trioxide, ammonium ortho tungstate, ammonium meta tungstate, ammonium paratungstate, sodium tungstate and potassium tungstate.

The diarylamines that may optionally be used and that have been found to be useful in this invention are well known antioxidants and there is no known restriction on the type of diarylamine that can be used. Preferably, the diarylamine has the formula:

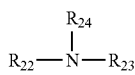

Wherein $R_{22}$ and $R_{23}$ each independently represents a substituted or unsubstituted aryl group having from 6 to 30 carbon atoms. Illustrative of substituents for the aryl group include aliphatic hydrocarbon groups such as alkyls having from 1 to 30 carbon atoms, hydroxy groups, halogen radicals, carboxylic acid or ester groups, or nitro groups. The aryl is preferably substituted or unsubstituted phenyl or naphthyl, particularly wherein one or both of the aryl groups are substituted with at least one alkyl having from 4 to 30 carbon atoms, preferably from 4 to 18 carbon atoms, most preferably from 4 to 12 carbon atoms. It is preferred that one or both aryl groups be substituted, e.g. mono-alkylated diphenylamine, di-alkylated diphenylamine, or mixtures of mono- and di-alkylated diphenylamines.

$R_{24}$ is hydrogen, $C_1$-$C_{12}$ alkyl, benzyl, allyl, methallyl, phenyl or a group —$CH_2SR_5$, where $R_5$ is $C_4$-$C_{18}$ alkyl, —$CH_2CH_2COO(C_4$-$C_{18}$ alkyl), or an alkylene, aralkylene bridging two amine moieties.

The diarylamines used in this invention can be of a structure other than that shown in the above formula that shows but one nitrogen atom in the molecule. Thus the diarylamine can be of a different structure provided that at least one nitrogen has 2 aryl groups attached thereto, e.g. as in the case of various diamines having a secondary nitrogen atom as well as two aryl groups bonded to one of the nitrogen atoms.

The diarylamines used in this invention should be soluble in the formulated crankcase oil package. Examples of some diarylamines that may be used in this invention include diphenylamine; alkylated diphenylamines; 3-hydroxydiphenylamine; N-phenyl-1,2-phenylenediamine; N-phenyl-1,4-phenylenediamine; monobutyldiphenylamine; dibutyldiphenylamine; monooctyldiphenylamine; dioctyldiphenylamine; monononyldiphenylamine; dinonyldiphenylamine; monotetradecyldiphenylamine; ditetradecyldiphenylamine; phenyl-alpha-naphthylamine; monooctyl phenyl-alpha-naphthylamine; phenyl-beta-naphthylamine; monoheptyldiphenylamine; diheptyldiphenylamine; p-oriented styrenated diphenylamine; mixed butyloctyldiphenylamine; and mixed octylstryryldiphenylamine, and mixtures thereof. Examples of commercial diarylamines include, for example, IRGANOX™ L06, IRGANOX™ L57 (mixed butyloctyl diphenyl amine) and I IRGANOX™ L67 from Ciba Specialty Chemicals; NAUGALUBE™ AMS, NAUGALUBE™ 438, NAUGALUBE™ 438R, NAUGALUBE™ 438L, NAUGALUBE™ 500, NAUGALUBE™ 640, NAUGALUBE™ 680, and NAUGARD PANA™ from Crompton Corporation; GOODRITE™ 3123, GOODRITE™ 3190X36, GOODRITE™ 3127, GOODRITE™ 3128, GOODRITE™ 3185X1, GOODRITE™ 3190X29, GOODRITE™ 3190X40, GOODRITE™ 3191 and GOODRITE™ 3192 from Noveon Specialty Chemicals; VANLUBE™ DND, VANLUBE™ NA, VANLUBE™ PNA, VANLUBE™ SL (mixed octylstyryl diphenylamine), VANLUBE™ SLUP, VANLUBE™ SS, VANLUBE™ 81, VANLUBE™ 848, and VANLUBE™ 849, VANLUBE™ 961 (mixed butyloctyl diphenyl amine) from R. T. Vanderbilt Company Inc, LUBRIZOL™ 5150A & C from LUBRIZOL™, and NA-LUBE™ AO-140 (mixed butyloctyl diphenyl amine), NA-LUBE™ AO-150 (mixed octylstyryl diphenylamine), from King Industries.

7. Organoamine Tungstates with Amines Containing Other Stabilizing Moieties

The organoamine tungstate compounds useful in the present invention may be prepared by a variety of methods. One method involves reacting a sulfur and phosphorus-free tungsten source with an alkylated triazole, or a phenolic antioxidant. Examples of sulfur- and phosphorus-free tungsten sources include tungstic acid, tungsten trioxide, ammonium ortho tungstate, ammonium meta tungstate, ammonium paratungstate, sodium tungstate and potassium tungstate.

A triazole having the formula

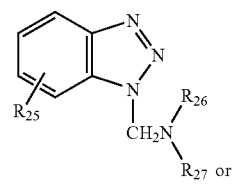

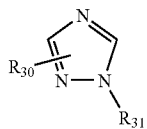

wherein $R_{25}$ is hydrogen or a $C_1$-$C_{20}$ alkyl residue; $R_{26}$ and $R_{27}$ are the same or different and each is H, $C_1$-$C_{20}$ alkyl, $C_3$-$C_{20}$ alkenyl, $C_5$-$C_{12}$ cycloalkyl, $C_7$-$C_{13}$ aralkyl, $C_6$-$C_{10}$ aryl or $R_{26}$ and $R_{27}$, together with the nitrogen atom to which they are attached, form a 5-, 6- or 7-membered heterocyclic residue or $R_{26}$ and $R_{27}$ is each a residue of formula:

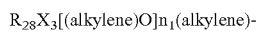

wherein $X_3$ is O, S or $N(R_{28})$, $R_{28}$ is hydrogen or $C_1$-$C_{20}$ alkyl, "alkylene" is a $C_1$-$C_{12}$ alkylene residue and $n_1$ is an integer from 0 to 6;

$R_{30}$ is hydrogen, $C_1$-$C_{20}$ alkyl or $C_6$-$C_{10}$ aryl or $C_7$-$C_{18}$ alkyl phenyl; and $R_{31}$ is hydrogen, $C_1$-$C_{20}$ alkyl or a residue —$CH_2$ $NR_{26}R_{27}$ wherein $R_{26}$ and $R_{27}$ have their previous significance or $R_{26}$ has its previous significance and $R_{27}$ is a residue of formula

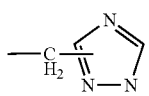

I or $R_{27}$ is a residue of formula as defined above and $R_{26}$ is a residue of formula

in which $m_1$ is 0 or 1, and when $m_1$ is 0, A is a residue of formula (I) and when $m_1$ is 1, A is alkylene or $C_6$-$C_{10}$ arylene, and alkylene and $n_1$ have their previous significance and $R_{32}$ is a residue of formula I, as defined above.

A substituted phenol of the formula

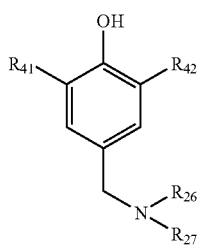

wherein, $R_{42}$, are independently alkyl of 1 to 18 carbon atoms, cycloalkyl of 5 to 6 carbon atoms, phenyl, phenyl substituted by alkyl of 1 to 18 carbon atoms, aralkyl of 7 to 9 carbon atoms or said aralkyl substituted by alkyl of 1 to 18 carbon atoms. $R_{26}$ and $R_{27}$ are the same or different and each is H, $C_1$-$C_{20}$ alkyl, $C_3$-$C_{20}$ alkenyl, $C_5$-$C_{12}$ cycloalkyl, $C_7$-$C_{13}$ aralkyl, $C_6$-$C_{10}$ aryl or $R_{26}$ and $R_{27}$, together with the nitrogen atom to which they are attached, form a 5-, 6- or 7-membered heterocyclic residue or $R_{26}$ and $R_{27}$ is each a residue of formula:

wherein $X_3$ is O, S or $N(R_{28})$, $R_{28}$ is hydrogen or $C_1$-$C_{20}$ alkyl, "alkylene" is a $C_1$-$C_{12}$ alkylene residue and $n_1$ is 0 or an integer from 1 to 6.

8.0 Organoamine Tungstates from Polyamine Salts

The organoamine tungstate compounds useful in the present invention may be prepared by a variety of methods. One method involves reacting a sulfur and phosphorus-free tungsten source with an amine, carboxylate, sulfonate, dithiophosphate, naphthenates, phosphonates, phenoxy alkanoates, and N-acyl sarcosinates. Examples of sulfur- and phosphorus-free tungsten sources include tungstic acid, tungsten trioxide, ammonium ortho tungstate, ammonium meta tungstate, ammonium paratungstate, sodium tungstate and potassium tungstate.

A soluble acid salt of a carboxylic acid, a mono or disulfonic acid, naphthenic acid, dithiophosphoric acid or alkyl phosphonic acid with a polyamine is prepared in the first step and subsequently reacted with various tungsten sources as outlined above to the desired tungstate, which are oil soluble In certain embodiments, long-chain monocarboxylic acids suitable for use in the present invention preferably contain at least 8, and more preferably at least 12, and up to 100 carbon atoms. In preferred embodiments, examples of suitable acids for use in the present invention include fatty acids such as coconut acid, hydrogenated coconut acid, menhaden acid, hydrogenated menhaden acid, tallow acid, hydrogenated tallow acid, and soya acid. Additional long-chain carboxylic acids that may be used include lauric acid, myristic acid, palmitic acid, stearic acid, isostearic acid, arachidic acid, behenic acid, erucic acid, oleic acid, linoleic acid, and linolenic acid. Mixtures of acids may also be used and are sometimes preferred. For example, commercial oleic acid is actually a mixture of many fatty acids ranging in carbon chain length from 14 to 20.

The sulfonic acid of the current invention could be one of the following:

1) An alkylated aryl sulfonic acid selected from the group consisting of

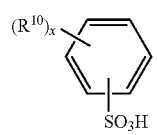

wherein $R^{10}$ is H or an alkyl group containing up to 20 carbon atoms, and x is an integer from 0 to 2.

An alkylated aryl sulfonic acid selected from the group consisting of

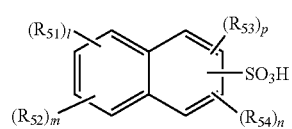

wherein $R_{51}$, $R_{52}$, $R_{53}$ and $R_{54}$ are individually selected from the group consisting of hydrogen or essentially linear hydrocarbyl groups having about 9 to about 22 carbon atoms; and wherein l, m, n and p are integers from 0 to 4 and the sum of l+m+n+p is at least 1; and wherein $R_{51}$, $R_{52}$, $R_{53}$ and $R_{54}$ is a hydrogen where either l, m, n, or p is 0.

2) An alkylated aryl disulfonic acid selected from the group consisting of

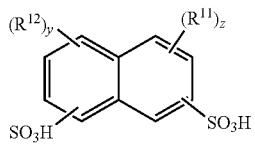

and structure II

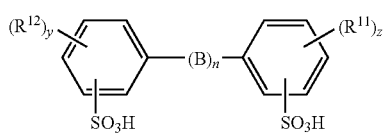

wherein each of $R^{11}$ and $R^{12}$ is the same or different and is a linear or branched alkyl group with 6 to 16 carbons, y is 0 to 3, z is 0 to 3 with the proviso that y+z is 1 to 4, n is 0 to 3, B is a divalent moiety selected from the group consisting of —$C(R^{13})(R^{14})$—, wherein each of $R^{13}$ and $R^{14}$ is H or independently a linear or branched alkyl group of 1-4 carbons and n is 1; —C(=O)—, wherein n is 1; —O— wherein n is 1; —S—, wherein n is 1 to 3; and —$SO_2$—, wherein n is 1;

Suitable sulfonic acids include alkane sulfonic acid, aralkyl sulfonic acid, including dodecyl benzene sulfonic acid, didodecyl benzenesulfonic acid, and sulfonic acids derived from various hydrocarbon feedstock. Examples of other suitable sulfonic acids include mono-, di-, and polyalkylated naphthalenesulfonic acids, e.g., dinonyl napthalene sulfonic acid, didodecyl naphthalene sulfonic acids, diphenyl ether sulfonic acid, napthalene disulfide sulfonic acid, dicetyl thianthrene sulfonic acid, dialauryl betanaphthol sulfonic acid, dicapryl nitronaphthalene sulfonic acid, unsaturated paraffin wax sulfonic acid, hydroxy substituted paraffin wax sulfonic acid, tetraamylene sulfonic acid, mono- and polychloro substituted paraffin wax sulfonic acid, nitrosoparaffin wax sulfonic acid, cycloaliphatic sulfonic acid such as laurylcyclohexyl sulfonic acid, mono- and poly-wax-substituted cyclohexyl sulfonic acid, and the like. Suitable acid components include naphthenic acid, which encompasses a mixture of monobasic acids of cycloparaffins which are derived from either cyclopentane or cyclohexane and cyclopentane and a great variety of homologs and higher molecular weight analogs. Conventionally, the acids of commercial mixtures of naphthenic acids have molecular weights in the range of from about 180 to 350. Suitable acid components include dihydrocarbylphosphoric acids, dihydrocarbyldithiophosphoric acids, and dihydrocarbylmonothiophosphoric acids, from the following

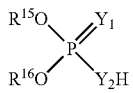

wherein $Y_1$ and $Y_2$ are each independently of the other S or O $R^{15}$ and $R^{16}$ are each independently of the other H, $C_3$-$C_{18}$ alkyl, $C_5$-$C_{12}$ cycloalkyl, $C_5$-$C_6$ cycloalkylmethyl, $C_9$-$C_{10}$ bicycloalkylmethyl, $C_9$-$C_{10}$ tricycloalkylmethyl, phenyl, $C_7$-$C_{24}$-alkylphenyl, or $R^{15}$ and $R^{16}$ together are the group of the partial formula:

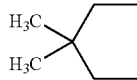

$R^{15}$ and $R^{16}$ defined as $C_9$-$C_{10}$ bicycloalkylmethyl are typically decalinylmethyl. $R^{15}$ and $R^{16}$ defined as $C_9$-$C_{10}$ tricycloalkylmethyl are preferably a group of formula:

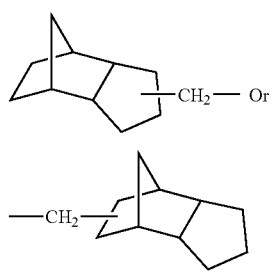

$R^{15}$ and $R^{16}$ are preferably i-propyl, i-butyl, 2-ethylhexyl, octyl phenyl or oleyl. Suitable acid components also include an alkyl phenoxyalkanoic acid of the formula

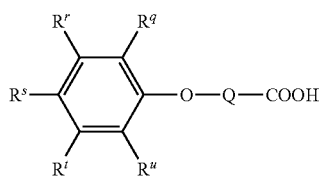

wherein $R^q$, $R^r$, $R^s$, $R^t$ and $R^u$ are, each independently of the other, hydrogen or $C_1$-$C_{20}$ alkyl and Q is a divalent $C_1$-$C_{20}$ hydrocarbon radical, saturated or unsaturated, selected from the group consisting of

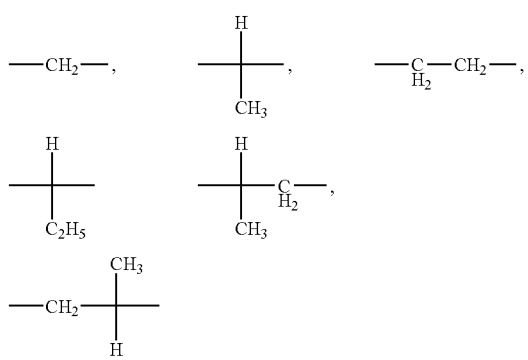

Suitable acid components also include an N-acyl sarcosine derivative of the formula

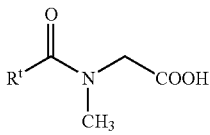

wherein the acyl group R'—C(=O)— is the residue of a fatty acid having 10 to 20 carbon atoms.

The polyamine compounds which may be employed in the production of the oil-soluble tungstate can be any suitable polyamine compound. In order to improve solubility of the organo tungstate product in base oils and finished oils, it is important for the mono-substituted diamine to have a high hydrocarbon character. For example, the diamine can be represented by the following general structure:

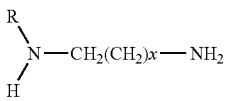

where x is 1 or 2, and R is a hydrocarbon-containing group containing a minimum of about 6 carbon atoms and up to 24 carbon atoms. R can be aliphatic or aromatic. R, in addition to the minimum of about 6 carbon atoms, may also contain oxygen, but preferably R does not include sulfur or additional nitrogen. It is preferred that R contains a minimum of 10 carbon atoms in order to further improve the organotungsten product solubility in base oil. The most preferred R contains oxygen in addition to the carbons, such as where R is an alkyloxyalkylene group. Where R represents an alkyloxyalkylene group, R can be represented by the structure —$X_1$—O—$X_2$, where $X_1$ is an alkylene of 2, 3 or 4 carbons and preferably is propylene or ethylene, and $X_2$ is an alkyl moiety having 3 to 30 carbon atoms, more preferably an alkyl moiety having 7 to 20 carbon atoms, and where X 2 can be a straight or branched, saturated or partially unsaturated hydrocarbon chain. The use of a diamine including an R group represented by —$X_1$—O—$X_2$ as defined herein in the reaction process makes it possible to maximize the level of tungsten incorporation levels in the oil soluble reaction product while performing the process without the use of volatile organic processing solvents.

Examples of some mono-substituted diamines that may be used include phenylaminopropylamine, hexylaminopropylamine, benzylaminopropylamine, octylaminopropylamine, octylaminoethylamine, dodecylaminopropylamine, dodecylaminoethylamine, hexadecylaminopropylamine, hexadecylaminoethylamine, octadecylaminopropylamine, octadecylaminoethylamine, isopropyloxypropyl-1,3-diaminopropane, octyloxypropyl-1,3-diaminopropane, decyloxypropyl-1,3-diaminopropane, isodecyloxypropyl-1,3-diaminopropane, dodecyloxypropyl-1,3-diaminopropane, tetradecyloxypropyl-1,3-diaminopropane, isodecyloxypropyl-1,3-diaminopropane, isododecyloxypropyl-1,3-diaminopropane, isotridecyloxypropyl-1,3-dia-minopropane. Mono-substituted diamines derived from fatty acids may also be used. Examples include N-coco alkyl-1,3-propanediamine (Duomeen C), N-tallow alkyl-1,3-propanediamine (Duomeen T), and N-oleyl-1,3-propanediamine (Duomeen OL), all obtained from Akzo Nobel.

Especially preferred polyamine compounds include diamine 1,3-diaminopropane having an alkyl moiety selected from the group consisting of N-coco, N-tallow, N-soya and N-oleyl. The compound 1,3-diaminopropane can be represented by the general formula R—NH($C_3H_6NH_2$) wherein R is an alkyl group representing the coco, tallow, soya or oleyl moiety.

Other suitable polyamines include tetraethylene pentamine and similar polyamine types containing primary and/or secondary amine groups. Further suitable polyamines can be represented by the general formulas R($NH_2$)$_2$ and R NH—($C_3H_6NH_2$)$_2$ wherein R is an alkyl radical derived from the dimerization of a $C_{18}$ unsaturated fatty acid. Another group of suitable polyamine compounds can be represented by the general formula R—N—($C_3H_6NH_2$)$_2$ wherein R is an alkyl radical derived from tallow, oleyl and lauryl fatty acids.

Other useful amine compounds include alicyclic diamines such as 1,4-di-(aminomethyl)cyclohexane, and heterocyclic nitrogen compounds such as imidazolines, and N-aminoalkyl piperazines of the general formula:

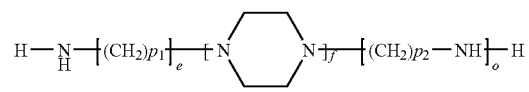

wherein $p_1$ and $p_2$ are the same or different and each is an integer from 1 to 4, and e, f and o are the same or different and each is an integer from 1 to 3.

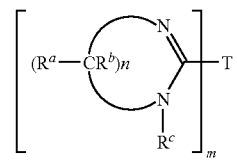

in which n=2 or 3, m=1 or 2, $R^a$, $R^b$ and $R^c$ are identical or different, and represent hydrogen, alkyl, or substituted alkyl, hydroxyalkyl, aryl, aralkyl, cycloalkyl, heterocyclics, ether, thioether, halogen, —N(R)$_2$, polyethylene polyamines, nitro groups, keto groups, ester groups, or carbonamide groups, alkyl substituted with the various functional groups described above, and T represents alkyl, alkylene, aryl, aralkyl, cycloalkyl or heterocyclic radical, substituted if desired with halogen, nitro groups, alkyl groups, alkoxy groups or amino groups, and, when m=1, represents also hydrogen. Salts of the above structures include carboxylic including aliphatic, aromatic and poly carboxylic, carbonic, sulfonic and phosphoric acid salts.

$R^a$, $R^b$, $R^c$ are independently hydrogen, alkyl, alkenyl or alkoxy of 1 to 36 carbons, cycloalkyl of 6 to 32 carbons or alkylamino of 1 to 36 carbon atoms, cycloalkyl of 5 to 12 carbon atoms, phenyl, hydroxyalkyl or hydroxycycloalkyl of 1 to 20 carbon atoms, methoxyalkyl of 1 to 20 carbon atoms, aralkyl of 7 to 9 carbon atoms, where the aryl group of the aralkyl group is further substituted by alkyl of 1 to 36 carbon atoms.

When m=2, T is alkylene of 1 to 12 carbons or arylene of 6 to 10 carbons, or a plurality of radicals being able to be joined, containing hetero atoms also by hetero atoms such as O, N or S, if desired. Preferred imidazoline structures are where R is a long chain alkyl up to 18 carbon atoms, m=1 and $R^c$ is one of 2-hydroxyethyl, or 2-aminoethyl or 2-amido ethyl substituents.

Examples of such amines include 2-pentadecyl imidazoline, aminoethyl oleyl imidazoline and N-(2-aminoethyl)piperazine.

Ammonium molybdates derived from these precursor salts that are a component of the present invention may also be prepared from a molybdenum source. The process for preparing the organoammonium molybdates of the invention involves the use of one of several molybdenum sources including molybdenum trioxide, ammonium paramolybdate or ammonium heptamolybdate. A preferred molybdenum source is molybdenum trioxide. The use of molybdenum trioxide results in effective molybdenum incorporation into the organic ligand made by the aforementioned first process step, and it produces a reaction mass by the completion of the second step that does not require filtration.

9.0 Organoammonium Tungstates from the Reaction Product of Mono Carboxylic Acid with Diamines, Fatty Oil with Diamines and Naphthenyl, Alkylphenoxyalkanoyl and N-Sarcosoyl Polyamines.

The organoamine tungstate compounds useful in the present invention may be prepared by a variety of methods. One method involves reacting a sulfur and phosphorus-free tungsten source with the reaction product of a mono carboxylic acid, fatty oil, vegetable oil, triglyceride or glycerol esters of fatty acids, naphthenic acid, alkylphenoxy alkanoic acid or N-acyl sarcosine with a monosubstituted alkylene diamine. Examples of sulfur- and phosphorus-free tungsten sources include tungstic acid, tungsten trioxide, ammonium ortho tungstate, ammonium meta tungstate, ammonium paratungstate, sodium tungstate and potassium tungstate.

In certain embodiments, examples of long-chain monocarboxylic acids suitable for use in the present invention preferably contain at least 8, and more preferably at least 12, and up to 100 carbon atoms. In preferred embodiments, examples of suitable acids for use in the present invention include fatty acids such as coconut acid, hydrogenated coconut acid, menhaden acid, hydrogenated menhaden acid, tallow acid, hydrogenated tallow acid, and soya acid. Additional long-chain carboxylic acids that may be used include lauric acid, myristic acid, palmitic acid, stearic acid, isostearic acid, arachidic acid, behenic acid, erucic acid, oleic acid, linoleic acid, and linolenic acid. Mixtures of acids may also be used and are sometimes preferred. For example, commercial oleic acid is actually a mixture of many fatty acids ranging in carbon chain length from 14 to 20.

Examples of preferred fatty or vegetable oils that may be used in the process of the present invention include groundnut oil, coconut oil, linseed oil, palm kernel oil, olive oil, cottonseed oil, grapeseed oil, corn oil, canola oil, palm oil, peanut oil, safflower seed oil, sesame seed oil, caster oil, rapeseed oil (low or high erucic acids), soyabean oil, sunflower oil, herring oil, sardine oil, lard, menhaden oil, hazel nut oil, walnut oil, and tallow, and mixtures thereof. These fatty or vegetable oils can include those compounds generally known as triglycerides, which have the general structure as shown below

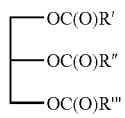

where R', R'', or R''' independently represent saturated or unsaturated aliphatic hydrocarbon groups having from about 8 to about 22 carbon atoms, and preferably are hydrocarbon chains having about 12 to about 22 carbon atoms. Mono- and diglycerides, either separately or in mixtures with one or more triglycerides, are also useful as fatty or vegetable oils in the present invention, in which the R', R'', or R''' groups present have the same above meaning.

Suitable acid components include naphthenic acid, which encompasses a mixture of monobasic acids of cycloparaffins which are derived from either cyclopentane or cyclohexane and cyclopentane and a great variety of homologs and higher molecular weight analogs. Conventionally, the acids of commercial mixtures of naphthenic acids have molecular weights in the range of from about 180 to 350.

Suitable acid components also include an alkyl phenoxyalkanoic acid of the formula

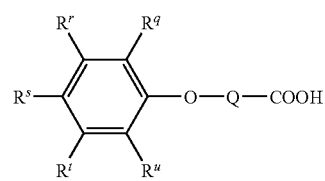

wherein $R^q$, $R^r$, $R^s$, $R^t$ and $R^u$ are, each independently of the other, hydrogen or $C_1$-$C_{20}$ alkyl and Q is a divalent $C_1$-$C_{20}$ hydrocarbon radical, saturated or unsaturated, selected from the group consisting of

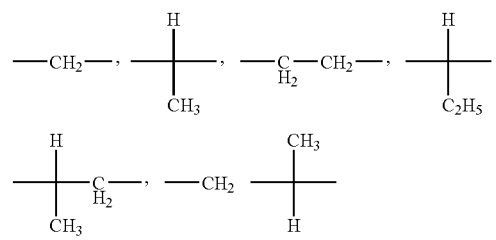

Suitable acid components also include an N-acyl sarcosine derivative of the formula

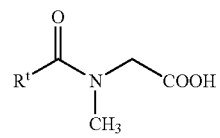

wherein the acyl group $R^t$—C(=O)— is the residue of a fatty acid having 10 to 20 carbon atoms.

The polyamine compounds which may be employed in the production of the oil-soluble sulfonate tungstate can be any suitable polyamine compound. In order to improve solubility of the organo tungstate product in base oils and finished oils, it is important for the mono-substituted diamine to have a high hydrocarbon character. For example, the diamine can be represented by the following general structure:

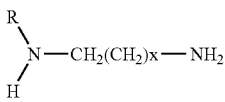

where x is 1 or 2, and R is a hydrocarbon-containing group containing a minimum of about 6 carbon atoms and up to 24 carbon atoms. R can be aliphatic or aromatic. R, in addition to the minimum of about 6 carbon atoms, may also contain oxygen, but preferably R does not include sulfur or additional nitrogen. It is preferred that R contains a minimum of 10 carbon atoms in order to further improve the organotungsten product solubility in base oil. The most preferred R contains oxygen in addition to the carbons, such as where R is an alkyloxyalkylene group. Where R represents an alkyloxyalkylene group, R can be represented by the structure —$X_1$—O—$X_2$, where $X_1$ is an alkylene of 2, 3 or 4 carbons and preferably is propylene or ethylene, and $X_2$ is an alkyl moiety having 3 to 30 carbon atoms, more preferably an alkyl moiety having 7 to 20 carbon atoms, and where X 2 can be a straight or branched, saturated or partially unsaturated hydrocarbon chain. The use of a diamine including an R group represented by —$X_1$—O—$X_2$ as defined herein in the reaction process makes it possible to maximize the level of tungsten incorporation levels in the oil soluble reaction product while performing the process without the use of volatile organic processing solvents.

Examples of some mono-substituted diamines that may be used include phenylaminopropylamine, hexylaminopropylamine, benzylaminopropylamine, octylaminopropylamine, octylaminoethylamine, dodecylaminopropylamine, dodecylaminoethylamine, hexadecylaminopropylamine, hexadecylaminoethylamine, octadecylaminopropylamine, octadecylaminoethylamine, isopropyloxypropyl-1,3-diaminopropane, octyloxypropyl-1,3-diaminopropane, decyloxypropyl-1,3-diaminopropane, isodecyloxypropyl-1,3-diaminopropane, dodecyloxypropyl-1,3-diaminopropane, tetradecyloxypropyl-1,3-diaminopropane, isodecyloxypropyl-1,3-diaminopropane, isododecyloxypropyl-1,3-diaminopropane, isotridecyloxypropyl-1,3-diaminopropane. Mono-substituted diamines derived from fatty acids may also be used. Examples include N-coco alkyl-1,3-propanediamine (Duomeen C), N-tallow alkyl-1,3-propanediamine (Duomeen T), and N-oleyl-1,3-propanediamine (Duomeen OL), all obtained from Akzo Nobel. Especially preferred are polyamine compounds including diamine 1,3-diaminopropane having an alkyl moiety selected from the group consisting of N-coco, N-tallow, N-soya and N-oleyl. The compound 1,3-diaminopropane can be represented by the general formula R—NH($C_3H_6NH_2$) wherein R is an alkyl group representing the coco, tallow, soya or oleyl moiety.

Other suitable polyamines include tetraethylene pentamine and similar polyamine types containing primary and/or secondary amine groups. Further suitable polyamines can be represented by the general formulas R($NH_2$)$_2$ and R NH—($C_3H_6NH_2$)$_2$ wherein R is an alkyl radical derived from the dimerization of a $C_{18}$ unsaturated fatty acid. Another group of suitable polyamine compounds can be represented by the general formula R—N—($C_3H_6NH_2$)$_2$ wherein R is an alkyl radical derived from tallow, oleyl and lauryl fatty acids.

10.0 Organoammonium Tungstates from the Reaction Product of Substituted Succinic Anhydrides with Polyamines The organoamine tungstate compounds useful in the present invention may be prepared by a variety of methods. One method involves reacting a sulfur and phosphorus-free tungsten source with the reaction product of substituted succinic anhydrides with polyamines. Examples of sulfur- and phosphorus-free tungsten sources include tungstic acid, tungsten trioxide, ammonium ortho tungstate, ammonium meta tungstate, ammonium paratungstate, sodium tungstate and potassium tungstate.

Succinimides of the current invention may be represented by the following general formula.

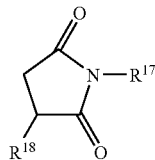

where $R^{18}$ is a C6 to C30 isomerized alkenyl group, represented by:

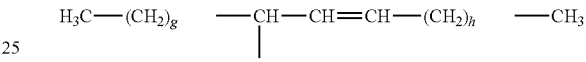

(where g and h are integers whose sum is from 1 to 25), or its fully saturated alkyl analog, $R^{17}$ is an alkyl group, aryl group, containing one or more nitrogen atom and other heteroatoms.

The succinimides of the present invention are those produced from succinic anhydrides substituted with isomerized alkenyl groups or their fully saturated alkyl analogs. Preparation of isomerized alkenyl succinic anhydrides is described in, for example, U.S. Pat. No. 3,382,172, hereby incorporated by reference in its entirety.

Often these materials are prepared by heating alpha-olefins with acidic catalysts to migrate the double bond to form an internal olefin. This mixture of olefins (2-enes, 3-enes, etc.) is then thermally reacted with maleic anhydride.

Typically olefins from $C_6$ (e.g. 1-hexene) to $C_{30}$ (e.g. 1-tricosane) are used. Suitable isomerized alkenyl succinic anhydrides of structure (1)

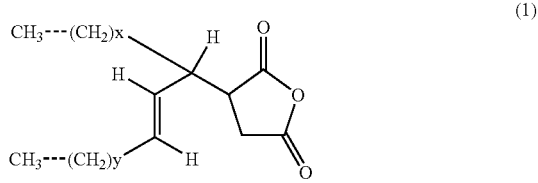

(1)

include isodecylsuccinic anhydride (x+y=5), iso-dodecyisuccinic anhydride (x+y=7), iso-tetradecylsuccinic anhydride (x+y=9), iso-hexadecylsuccinic anhydride (x+y=11), iso-octadecylsuccinic anhydride (x+y=13) and isoeicosylsuccinic anhydride (x+y=15). Preferred materials are isohexadecylsuccinic anhydride and iso-octadecylsuccinic anhydride.

The materials produced by this process contain one double bond (alkenyl group) in the alkyl chain. The alkenyl substituted succinic anhydrides may be easily converted to their saturated alkyl analogs by hydrogenation.

Suitable primary and secondary amines useful to produce the succinimides are represented by structure

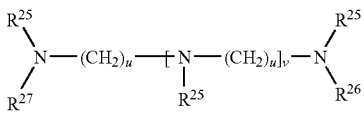

where $R^{25}$, $R^{26}$, and $R^{27}$ are independently selected from the group consisting of H, $C_1$ to $C_{25}$ straight or branched chain alkyl radicals, $C_1$ to $C_{12}$ alkoxy radicals; $C_2$ to $C_6$ alkylene radicals; u is an integer from 1 to 6, preferably 2 to 4; and v is an integer from 0 to 10, preferably from 1 to 4.

Bis succinimides of the current invention may be represented by the following general formula

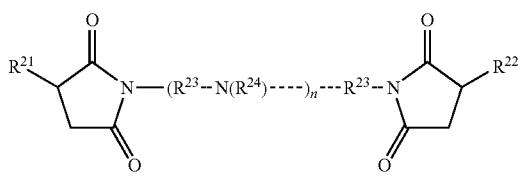

wherein, $R^{21}$ and $R^{22}$ may be identical or different from each other and are each hydrocarbon groups having 5 or more carbons; $R^{23}$ is a divalent hydrocarbon group having 1 to 5 carbons; $R^{24}$ is a hydrogen atom or a hydrocarbon group having 1 to 20 carbons; and n is an integer in the range of 0 to 10. In the above general formula, $R^{21}$ and $R^{22}$ may be the same as each other or different from each other, and are each saturated or unsaturated hydrocarbon groups having 5 or more carbons, preferably 5 to 40 carbons. Examples of hydrocarbon groups include pentyl groups, hexyl groups, heptyl groups, octyl groups, nonyl groups, decyl groups, dodecyl groups, tridecyl groups, tetradecyl groups, pentadecyl groups, hexadecyl groups, heptadecyl groups, octadecyl groups, nonadecyl groups, oleyl groups and other hydrocarbon groups having up to 40 carbons. Preferred hydrocarbon groups include straight chain hydrocarbon groups having between 8 and 25 carbons. In the above general formula, $R^{23}$ is a divalent hydrocarbon group having 1 to 5 carbons, preferably an alkylene group having 2 or 3 carbons.

In the above general formula, $R^{24}$ is a hydrogen atom or a hydrocarbon group having 1 to 20 carbons. Examples of hydrocarbon groups include alkyl groups having 1 to 20 carbons; alkenyl groups having 2 to 20 carbons; cycloalkyl groups having 6 to 20 carbons; and aryl groups having 6 to 20 carbons. The aryl groups may have an alkyl group having 1 to 12 carbons. Hydrogen atoms and alkyl groups having 1 to 10 carbons are particularly preferred as $R^{24}$. Groups having a number of (i.e. 1 to 5 of each) amino groups and/or amide bonds in their structure can be used as the above-described hydrocarbon groups.

The amino groups are represented by —NH— or —$NH_2$; and the amide bonds are represented by

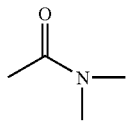

They may be bonded with the carbons of the hydrocarbon group at an arbitrary position.

The bis succinimides of the present invention are those produced from succinic anhydrides substituted with isomerized alkenyl groups or their fully saturated alkyl analogs, and polyamines. Suitable polyamines are saturated amines of the general formula:

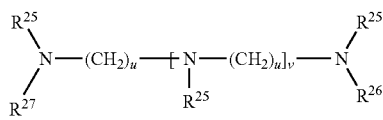

where $R^{25}$, $R^{26}$, and $R^{27}$ are independently selected from the group consisting of H, $C_1$ to $C_{25}$ straight or branched chain alkyl radicals, $C_1$ to $C_{12}$ alkoxy radicals; $C_2$ to $C_6$ alkylene radicals; u is an integer from 1 to 6, preferably 2 to 4; and v is an integer from 0 to 10, preferably from 1 to 4.

Non-limiting examples of suitable polyamine compounds include: 1,6-diaminohexane, diethylene triamine, triethylene tetramine, tetraethylene pentamine, and pentaethylene hexamine. Useful mixtures of polyamines having from 5 to 7 nitrogen atoms per molecule are available from Dow Chemical Co. as Polyamine H, Polyamine 400 and Polyamine E-300.

Polyoxyalkylene amines are also useful in this invention and are shown as structure

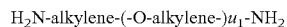

$H_2N$-alkylene-(-O-alkylene-)$u_1$-$NH_2$ where $u_1$ is an integer of from 1 to 10. The polyamines have molecular weights from about 100 to 500. The preferred polyoxyalkylene polyamines include polyoxyethylene and polyoxypropylene diamines and the polyoxypropylene triamines. Commercial polyoxyalkylene amines are available from Jefferson Chemical Co. sold under the trade name "Jeffamines D-230, D-400, D-1000, T-430," etc.

Organo ammonium molybdates derived from these precursor succinimides according to the invention may also be prepared from one of various molybdenum sources. The process for preparing the organoammonium molybdates of the invention involves the use of one of several molybdenum sources including molybdenum trioxide, ammonium paramolybdate or ammonium heptamolybdate. A preferred molybdenum source is molybdenum trioxide. The use of molybdenum trioxide results in effective molybdenum incorporation into the organic ligand made by the aforementioned first process step, and it produces a reaction mass by the completion of the second step that does not require filtration. There is no particular restriction on the type of secondary diarylamine used in the invention as an antioxidant. Preferably, the secondary diarylamine antioxidant has the general formula:

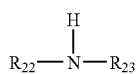

wherein $R_{22}$ and $R_{23}$ each independently represents a substituted or unsubstituted aryl group having from 6 to 30 carbon atoms. Illustrative of substituents for the aryl include aliphatic hydrocarbon groups such as alkyl having from about 1 to 20 carbon atoms, hydroxy, carboxyl or nitro, e.g., an alkaryl group having from 7 to 20 carbon atoms in the alkyl group. The aryl is preferably substituted or unsubstituted phenyl or naphthyl, particularly wherein one or both of the aryl groups are substituted with an alkyl such as one having from 4 to 30 carbon atoms, preferably from 4 to 18 carbon atoms, most preferably from 4 to 9 carbon atoms. It is further preferred that one or both aryl groups be substituted, e.g. mono alkylated diphenylamine, dialkylated diphenylamine, or mixtures of mono- and di-alkylated diphenylamines.

The secondary diarylamines used in this invention can be of a structure other than that shown in the above formula which shows but one nitrogen atom in the molecule. Thus, the secondary diarylamine can be of a different structure provided that at least one nitrogen has 2 aryl groups attached thereto, e.g., as in the case of various diamines having a secondary nitrogen atom as well as two aryls on one of the nitrogens. The secondary diarylamines used in this invention preferably have antioxidant properties in lubricating oils, even in the absence of the tungsten compound.

It is preferred that the oil-soluble secondary aromatic amines are diphenylamines of general formula:

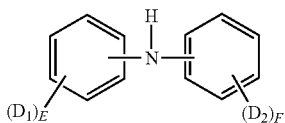

wherein $D_1$ and $D_2$ may be the same or different and each independently represents a hydrocarbyl radical as hereinbefore defined. It is preferred that $D_1$ and $D_2$ are $C_1$ to $C_{28}$ aliphatic hydrocarbyl radicals. E and F may be the same or different and may equal 0, 1, 2 or 3. It is preferred that E and F are the same and that they equal 1. It is also preferred that the diphenylamines have a nitrogen content of between 2.5 and 5% by weight. It is preferred that $D_1$ and $D_2$ are located in the meta or para positions relative to the amino substitution in the aromatic rings of the diphenylamines. Examples of suitable diphenylamines include di-octyldiphenylamine, t-pentyldiphenylamine, diisobornyldiphenylamine, didecyldiphenylamine, didodecyldiphenylamine, dihexyldiphenylamine, di-t-butyidiphenylamine, di-t-octyldiphenylamine, dinonylamine, dibutyldiphenylamine, distyryldiphenylamine. Other suitable diphenylamines include di-substituted derivatives wherein the $D_1$ and $D_2$ are different and independently represent hydrocarbyl radicals, such as t-butyl, t-octyl, styryl, n-butyl or n-octyl for example. Some of these diphenylamines are commercially available and are sold under the trademarks, VANLUBE™ DND, NAUGALUBE™ 438L, PEARSALL™ OA502, LUBRIZOL™ 5150A, VANLUBE™ SL, NAUGALUBE™ 680, INGANOX™ L-57 and VANLUBE™ 848. VANLUBE™ DND, NAUGALUBE™ 438L, PEARSALL™ OA502 and LUBRIZOL™ 5150A nominally have structures as represented by the above formula wherein $D_1$ and $D_2$ are $C_9$ hydrocarbyl groups and E=F=1. VANLUBE™ SL and NAUGALUBE™ 680 nominally have structures as represented by above formula wherein $D_1$ and $D_2$ are either one of $C_4$, $C_8$ or styryl hydrocarbyl groups and E=F=1; these are mixed diphenyl amines. IRGANOX™ L-57 and VANLUBE™ 848 nominally have structures as represented by above formula wherein $D_1$ and $D_2$ are either one of t-butyl or t-octyl groups and E=F=1.

Other secondary diarylamines used in this invention soluble in the formulated crankcase oil package include: diphenylamine; various alkylated diphenylamines; 3-hydroxydiphenylamine; N-phenyl-1,2-phenylenediamine; N-phenyl-1,4-phenylenediamine; monobutyldiphenylamine; dibutyldiphenylamine; monooctyldiphenylamine; mononyldiphenylamine; dinonyldiphenylamine; monotetradecyldiphenylamine; ditetradecyldiphenylamine; phenyl-alpha-naphthylamine; monooctyl phenyl-alpha-naphthylamine; phenyl-beta-naphthylamine; monoheptyldiphenylamine; diheptyldiphenylamine; p-oriented styrenated diphenylamine; mixed butyloctyldiphenylamine; and mixed octylstryryldiphenylamine, and mixtures thereof. Other examples of commercial diarylamines include, for example, IRGANOX™ L06, IRGANOX™ L57 (mixed butyloctyl diphenyl amine) and IRGANOX™ L67 from Ciba Specialty Chemicals; NAUGALUBE™ AMS, NAUGALUBE™ 438, NAUGALUBE™ 438R, NAUGALUBE™ 438L, NAUGALUBE™ 500, NAUGALUBE™ 640, NAUGALUBE™ 680, and NAUGARD™ PANA from Crompton Corporation; GOODRITE™ 3123, GOODRITE™ 3190X36, GOODRITE™ 3127, GOODRITE™ 3128, GOODRITE™ 3185X1, GOODRITE™ 3190X29, GOODRITE™ 3190X40, GOODRITE™ 3191 and GOODRITE™ 3192 from Noveon Specialty Chemicals; VANLUBE™ DND, VANLUBE™ NA, VANLUBE™ PNA, VANLUBE™ SL (mixed octylstyryl diphenylamine), VANLUBE™ SLHP, VANLUBE™ SS, VANLUBE™ 81, VANLUBE™ 848, and VANLUBE™ 849, VANLUBE™ 961 (mixed butyloctyl diphenyl amine) from R. T. Vanderbilt Company Inc, LUBRIZOL™ 5150A & C from LUBRIZOL™, and NA-LUBE™ AO-140 (mixed butyloctyl diphenyl amine), NA-LUBE™ AO-150 (mixed octylstyryl diphenylamine), from King Industries.

The concentration of the secondary diarylamine in the lubricating composition can vary from about 0.075 to 2.5 wt %, depending upon the application. A practical diarylamine use range in the lubricating composition is from about 750 parts per million to 5,000 parts per million (i.e. 0.075 to 0.5 wt %), preferably from 1,000 to 4,000 parts per million (ppm) and even more preferably from about 1,200 to 3,000 ppm Preferably, the quantity of tungsten is relation to the quantity of the secondary amine should be within a certain ratio. The quantity of tungsten should be about 0.020 to 0.6 parts by weight for each part by weight of the amine in the lubricating oil composition. Preferably, this ratio will be from about 0.040 to 0.40 parts of the tungsten per part of the amine and particularly about 0.05 to 0.3 parts of the tungsten per part of the amine. The total quantity of tungsten and amine can be provided by one or more than one tungsten or amine compound.

An alkylated phenothiazine suitable for this invention is preferably oil soluble or dispersible and preferably corresponds to the general formula below where the substituents $R_{11}$-$R_{14}$ could contain heteroatoms,

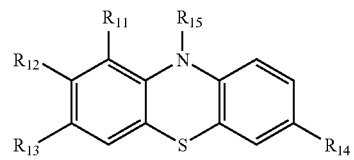

$R_{11}$ and $R_{12}$ are hydrogen or together form a fused six-membered aromatic ring; one of $R_{13}$ and $R_{14}$ is hydrogen and the other is $C_2$-$C_{30}$ alkyl, cyclo-$C_5$-$C_{12}$ alkyl, —$C_2$-$C_4$ alkyl, α-$C_1$-$C_2$ alkylbenzyl or α,α-dimethylbenzyl; or both $R_{13}$ and $R_{14}$ are $C_2$-$C_{30}$ alkyl, cyclo-$C_5$-$C_{12}$ alkyl-$C_2$-$C_4$ alkyl, α-$C_1$-$C_2$ alkylbenzyl or α,α-dimethylbenzyl, if $R_{11}$ and $R_{12}$ hydrogen; or $R_{13}$ is hydrogen and $R_{14}$ is $C_2$-$C_{30}$ alkyl, cyclo-$C_5$-$C_{12}$ alkyl$C_2$-$C_4$ alkyl, α-$C_1$-$C_2$ alkylbenzyl or α,α-dimethylbenzyl, if $R_{11}$ and $R_{12}$ together form a fused six-membered aromatic ring, $R_{15}$ is hydrogen, $C_1$-$C_{12}$ alkyl, benzyl, allyl, methallyl, phenyl or a group —$CH_2SR_4$, where $R_4$ is $C_4$-$C_{18}$ alkyl, —$CH_2CH_2COO(C_4$-$C_{18}$ alkyl), or an alkylene, aralkylene bridging two phenothiazine moieties.

Typical examples of alkylphenothiazine include but are not limited to monotetradecylphenothiazine, ditetradecylphenothiazine, monodecylphenothiazine, didecylphenothiazine, monononylphenothiazine, dinonylphenothiazine, monoctylphenothiazine and dioctylphenothiazine.

The antioxidant lubrication compositions of the present invention may optionally contain additional friction modifiers, antioxidants and/or copper corrosion inhibitors. Embodiments of friction modifiers which may optionally be added can be found for example in U.S. Pat. Nos. 4,792,410 and 5,110,488, which are incorporated herein by reference in their entirety and include fatty phosphites, fatty acid amides, fatty epoxides, borated fatty epoxides, fatty amines, glycerol esters, borated glycerol esters, alkoxylated fatty amines, borated alkoxylated fatty amines, metal salts of fatty acids, sulfurized olefins, fatty imidazolines and mixtures thereof.

Embodiments of antioxidants which may optionally be added include hindered phenolic antioxidants, secondary aromatic amine antioxidants, sulfurized phenolic antioxidants, oil-soluble copper compounds, phosphorus-containing antioxidants, organic sulfides, disulfides and polysulfides.

Embodiments of copper corrosion inhibitors which may optionally be added include thiazoles, triazoles and thiadiazoles. Example embodiments of such compounds include benzotriazole, tolyltriazole, octyltriazole, decyltriazole, dodecyltriazole, 2-mercapto benzothiazole, 2,5-dimercapto-1,3,4-thiadiazole, 2-mercapto-5-hydrocarbylthio-1,3,4-thiadiazoles, 2-mercapto-5-hydrocarbyldithio-1,3,4-thiadiazoles, 2,5-bis(hydrocarbylthio)-1,3,4-thiadiazoles, and 2,5-bis(hydrocarbyldithio)-1,3,4-thiadiazoles.

The organotungsten compound, alkylated diphenylamine and sulfur containing compound can either be added individually to a base oil to form the lubricating composition of the invention or they can be premixed to form a composition which can then be added to the base oil. The resulting lubricating composition preferably comprises a major amount (i.e. at least 90% by weight) of base oil and a minor amount (i.e. less than 10% by weight) of the additive composition.

In another aspect the invention provides for a lubricating oil composition which comprises lubricating oil and a lubricating oil additive comprising the combination of an oil-soluble tungsten compound and at least one oil-soluble aromatic amine. The concentration of the lubricating oil additive is typically in the range of 0.01 to about 15% by weight based on the total weight of the composition and is preferably from about 0.1 to about 7% by weight.

Suitable lubricating oils for use in preparing the lubricating composition include those oils which are conventionally employed as crankcase lubricating oils for internal combustion engines and those which may be employed as power transmitting fluids such as automatic transmission fluids, hydraulic fluids, or gear lubricants.

The lubricating oil may be a synthetic oil such as for example alkylesters of dicarboxylic acids, polyglycols and alcohols, polyalphaolefins, alkylbenzenes, alkyl naphthalenes, organic esters of phosphoric acids, or polysilicone oils. The lubricating oil may be a natural oil including mineral oils which may vary widely as to their crude source e.g. whether paraffinic, naphthenic or mixed paraffinic-naphthenic; as well as to their formation, e.g. distillation range, straight run or cracked, hydrorefined, or solvent extracted.

The invention further provides a lubricating oil concentrate. In the preparation of lubricating oil compositions it is a convenient practice to introduce additives in the form of a concentrate; which introduction may be made by methods known in the art. The lubricating oil concentrate may contain between 2.5 to 90 weight percent more preferably 5 to 75 weight percent of the additive composition in a suitable solvent. Suitable solvents may include hydrocarbon oils (e.g. mineral lubricating oil or synthetic oil).

The ratio of tungsten compound to the oil-soluble aromatic amine may be selected so as to provide an antioxidant effect of sufficient magnitude to meet the end use requirements of the lubricating oil—for example, to achieve adequate performance in the Sequence III E engine test for crankcase lubricating oils (according to the procedure of ASTM STP315). Preferably the tungsten compound and the oil-soluble aromatic amine are employed in a ratio of from 1:10 to 10:1 (by wt), more preferably from 3:1 to 1:3 (by wt).

The lubricating oil additive may be used as the sole additive for the composition or concentrate or may be used in combination with several different types of additives which may be required to fulfill other requirements of the composition or concentrate during use. The composition may be used as a crankcase lubricating oil, a cylinder lubricant for applications such as marine diesel, industrial oil, functional fluid such as power transmission fluid, tractor oil, gear oil or hydraulic fluid. Accordingly the compositions or concentrates of the invention may in addition to the lubricating oil additive contain one or more of the following:

(a) a dispersant, preferably an ashless dispersant;
(b) a metal containing detergent, preferably having a high total base number;
(c) an antiwear and/or extreme pressure additive;
(d) a viscosity index improver, which may also have dispersant properties;
(e) a pour point depressant;
(f) a corrosion inhibitor and/or metal deactivator; and
(g) a friction modifier or fuel economy agent, as well as other additives such as demulsifiers, seal swell agents, or even supplementary antioxidants.

Where such compositions are for use as crankcase lubricants they preferably contain at least an ashless dispersant and/or a viscosity index improver dispersant, a detergent, and an antiwear additive in amounts effective to provide their respective functions.

Dispersants

The preferred ashless dispersant in the compositions and concentrates of this invention is a long chain hydrocarbyl substituted mono- or di-carboxylic acid material, (i.e. acid, anhydride, or ester) and includes a long chain hydrocarbon, generally a polyolefin, substituted with an alpha or beta unsaturated C4 to C10 carboxylic acid material, such as itaconic acid, maleic acid, maleic anhydride, chloromaleic acid, dimethyl fumarate, chloromaleic anhydride, acrylic acid, methacrylic acid, crotonic acid, or cinnamic acid. Preferably, the dispersant contains at least about 1 mole (e.g. 1.05 to 1.2 moles, or higher) of the acid material per mole of polyolefin. The proportion of the dispersant is preferably from 1 to 10, and even more preferably 3 to 7 weight percent of the lubricating oil.

Preferred olefin polymers for the reaction with carboxylic acids are polymers derived from a C2 to C5 monoolefin. Such olefins include ethylene, propylene, butylene, isobutylene, pentene, oct-1-ene or styrene. The polymers may be homopolymers such as polyisobutylene or copolymers of two or more of such olefins. These include copolymers of ethylene and propylene; butylene and isobutylene; propylene and isobutylene; etc. Other copolymers include those in which a minor molar amount of the copolymer monomers (e.g. 1 to 10 mole percent), is a C4 to C18 diolefin, (e.g., a copolymer of isobutylene and butadiene; or a copolymer of ethylene, propylene and 1,4-hexadiene; etc).

In some cases, the olefin polymer may be completely saturated, for example an ethylene-propylene copolymer made by a Ziegler-Natta synthesis using hydrogen as a moderator to control molecular weight.

The olefin polymers usually have number average molecular weights above about 700, including number average molecular weights within the range of from 1,500 to 5,000 with approximately one double bond per polymer chain. An especially suitable starting material for a dispersant additive is polyisobutylene. The number average molecular weight for such polymers can be determined by several known techniques. A convenient method for such determination is by gel permeation chromatography (GPC) which additionally provides molecular weight distribution information. (see W. W. Yau, J. J. Kirkland and D. D. Bly, "Modern Size Exclusion Liquid Chromatography," John Wiley and Sons, New York, 1979).

Processes for the reaction of the olefin polymer with the unsaturated carboxylic acid, anhydride, or ester are known in the art. For example, the olefin polymer and the carboxylic acid material may be simply heated together as disclosed in U.S. Pat. Nos. 3,361,673 and 3,401,118 (hereby incorporated by reference in their entirety) to cause a thermal "ene" reaction to take place. Alternatively, the olefin polymer can be first halogenated, for example chlorinated or brominated, to about 1 to 8, preferably 3 to 7, weight percent chlorine or bromine, based on the weight of polymer, by passing chlorine or bromine through the polyolefin at a temperature of 100° C. to 250° C., e.g. 120° C. to 160° C., for about 0.5 to 10 hours, more preferably 1 to 7 hours. The halogenated polymer may then be reacted with sufficient unsaturated acid or anhydride at 100° to 250° C., usually 180° C. to 220° C., for 0.5 to 10 hours, more preferably 3 to 8 hours. Processes of this general type are taught in U.S. Pat. Nos. 3,087,436; 3,172,892; 3,272,746, hereby incorporated by reference in their entirety.

Alternatively, the olefin polymer and the unsaturated acid or anhydride are mixed and heated while chlorine is added to the hot material. Processes of this type are disclosed in U.S. Pat. Nos. 3,215,707; 3,231,587; 3,912,764; 4,110,349; 4,234,435; and GB-A-1 440 219, all of which are incorporated by reference in their entirety.

When a halogen is used, from 65 to 95 weight percent of the polyolefin normally reacts with the carboxylic acid or anhydride. Thermal reactions, carried out without the use of halogen or a catalyst, cause only from 50 to 75 weight percent of the polyisobutylene to react. Chlorination increases reactivity.

The carboxylic acid or anhydride can then be further reacted with amines, alcohols, including polyols, amino-alcohols, etc., to form other useful dispersant additives. Thus if the acid or anhydride is to be further reacted, (e.g. neutralized) then generally a major proportion of at least 50 percent of the acid units up to all the acid units will be reacted.

The ashless dispersants useful in this invention are polyisobutenyl succinimides formed from polyisobutenyl succinic anhydride and an alkylene polyamine such as triethylene tetramine or tetraethylene pentamine, wherein the polyisobutenyl substituent is derived from polyisobutene having a number average molecular weight preferably in the range of 700 to 1200 more preferably from 900 to 1100. It has been found that selecting certain dispersants within the broad range of alkenyl succinimides produces fluids with improved frictional characteristics. The most preferred dispersants of this invention are those wherein the polyisobutene substituent group has a molecular weight of approximately 950 atomic mass units, the basic nitrogen containing moiety is polyamine (PAM) and the dispersant has been post treated with a boronating agent.

The ashless dispersants of the invention can be used in any effective amount. However, they are typically used from about 0.1 to 10.0 mass percent in the finished lubricant, preferably from about 0.5 to 7.0 percent, and most preferably from about 2.0 to about 5.0 percent.

Useful amine compounds for reaction with the hydrocarbyl substituted carboxylic acid or anhydride include mono- and polyamines with preferably 2 to 60, and more preferably 3 to 20, total carbon atoms and from 1 to 12, and more preferably 2 to 8 nitrogen atoms in a molecule. These amines may be hydrocarbyl amines or may be hydrocarbyl amines including other groups, e.g. hydroxy groups, alkoxy groups, amide groups, nitriles, or imidazoline groups. Hydroxy amines with 1 to 6 hydroxy groups, preferably 1 to 3 hydroxy groups, are particularly useful. Preferred amines are aliphatic saturated amines, including those of the general formulae:

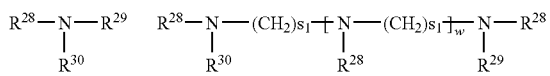

wherein $R^{28}$, $R^{29}$ and $R^{30}$ are each independently hydrogen; $C_1$ to $C_{25}$ straight or branched chain alkyl radicals; $C_1$ to $C_{12}$ alkoxy-($C_6$ alkylene) radicals; or $C_2$ to $C_{12}$ alkylamino-$C_2$ to $C_6$ alkylene) radicals; each $s_1$ can be the same or a different number of from 2 to 6, preferably 2 to 4; and w is a number from 0 to 10, preferably 2 to 7. Preferably at least one of $R^{28}$, $R^{29}$ and $R^{30}$ is hydrogen.

Suitable amines include 1,2-diaminoethane; 1,3-diaminopropane; 1,4-diaminobutane; 1,6-diaminohexane; polyethylene amines such as diethylene triamine; triethylene tetramine; tetraethylene pentamine; polypropylene amines such as 1,2-propylene diamine; di-(1,2-propylene)triamine; di(1,3-propylene)-triamine; N,N-dimethyl-1,3-diaminopropane; N,N-di-(2-aminoethyl)ethylene diamine; N,N-di(2-hydroxyethyl)-1,3-propylene diamine; 3-dodecyloxypropylamine; N-dodecyl-1,3-propane diamine; tris hydroxymethylaminomethane (THAM); diisopropanol amine; diethanol amine; triethanol amine; amino morpholines such as N-(3-aminopropyl)morpholine; etc.

Other useful amine compounds include alicyclic diamines such as 1,4-di-(aminomethyl)cyclohexane, and heterocyclic nitrogen compounds such as imidazolines, and N-aminoalkyl piperazines of the general formula:

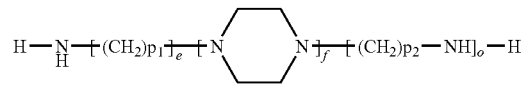

wherein $p_1$ and $p_2$ are the same or different and each is an integer from 1 to 4, and e, f and o are the same or different and each is an integer from 1 to 3. Examples of such amines include 2-pentadecyl imidazoline and N-(2-aminoethyl)piperazine.

Hydroxyamines which can be reacted with the long chain hydrocarbon substituted dicarboxylic acid material mentioned above to form dispersants include 2-amino-1-butanol, 2-amine-2-methyl-1-propanol, p-(beta-hydroxyethyl)- aniline, 2-amino-1-propanol, 3-amino-1-propanol, 2-amino-2-methyl-1,3-propanediol, 2-amino-2-ethyl-1,3-propanediol, N-(beta-hydroxy propyl)N'-(beta-aminoethyl)-piperazine, ethanolamine and beta-(beta-hydroxyethoxy)-ethylamine. Mixtures of these or similar amines can also be employed. Commercial mixtures of amine compounds may advantageously be used. For example, one process for preparing alkylene amines involves the reaction of an alkylene dihalide (such as ethylene dichloride or propylene dichloride) with ammonia, which results in a complex mixture of alkylene amines wherein pairs of nitrogens are joined by alkylene groups, forming such compounds as diethylene triamine, triethylene tetramine, tetraethylene pentamine and corresponding piperazines. Useful poly(ethyleneamine) compounds averaging about 5 to 7 nitrogen atoms per molecule are available commercially under trade names such as "Polyamine H", "Polyamine 400", "Dow Polyamine E-100", etc.

Useful amines also include polyoxyalkylene polyamines such as those of the formulae:

(i) $NH_2$-alkylene(O-alkylene)m $NH_2$ where m has a value of from 3 to 70, preferably 10 to 35; and (ii) R-(alkylene(O-alkylene)n NH2)3-6 where each n has a value of about 1 to 40, with the proviso that the sum of all the n's is from 3 to 70 and preferably from 6 to 35, and R is a saturated hydrocarbon radical of up to ten carbon atoms, wherein the number of substituents on the R group is from 3 to 6. The alkylene groups in either formula (i) or (ii) may be straight or branched chains containing about 2 to 7, and preferably about 2 to 4, carbon atoms.

The polyoxyalkylene polyamines above, preferably polyoxyalkylene diamines and polyoxyalkylene triamines, may have average molecular weights ranging from 200 to 4,000 and preferably from 400 to 2,000. The preferred polyoxyalkylene polyamines include the polyoxyethylene and polyoxypropylene diamines and the polyoxypropylene triamines having average molecular weights ranging from 200 to 2,000. The polyoxyalkylene polyamines are commercially available and may be obtained, for example, from the Jefferson Chemical Company, Inc. under the trade name "Jeffamines D-230, D400, D-1000, D-2000, T-403," etc.

The amine is readily reacted with the carboxylic acid material, e.g. alkenyl succinic anhydride, by heating an oil solution containing 5 to 95 weight percent of carboxylic acid material to from 100 to 250° C., preferably 125 to 175° C., generally for 1 to 10 hours, more preferably from 2 to 6 hours, until the desired amount of water has been removed. The heating is preferably carried out to favor formation of imides, or mixtures of imides and amides, rather than amides and salts. Reaction ratios can vary considerably, depending upon the reactants, amounts of excess amine, type of bonds formed, etc. Generally from 0.3 to 2 moles of amine, more preferably from 0.3 to 1.0 moles of amine, and even more preferably 0.4 to 0.8 mole of amine (e.g. bis-primary amine) is used per mole of the carboxylic acid moiety content (e.g. grafted maleic anhydride content). For example, one mole of olefin reacted with sufficient maleic anhydride to add 1.10 mole of maleic anhydride groups or mole of olefin when converted to a mixture of amides and imides, about 0.55 moles of amine with two primary groups would preferably be used, i.e. 0.50 mole of amine per mole of dicarboxylic acid moiety.

The nitrogen-containing dispersant can be further treated by boration as generally taught in U.S. Pat. Nos. 3,087,936 and 3,254,025, hereby incorporated by reference in their entirety.

Tris(hydroxymethyl)amino methane (THAM) can be reacted with the aforesaid acid material to form amides, imides or ester type additives as taught by GB-A-984 409, or to form oxazoline compounds and borated oxazoline compounds as described, for example, in U.S. Pat. Nos. 4,102,798, 4,116,876 and 4,113,639, hereby incorporated by reference in their entirety.

The ashless dispersants may also be esters derived from the long chain hydrocarbyl substituted carboxylic acid material and from hydroxy compounds such as monohydric and polyhydric alcohols or aromatic compounds such as phenols and naphthols, etc. The polyhydric alcohols are the most preferred hydroxy compound and preferably contain from 2 to 10 hydroxy radicals, for example, ethylene glycol, diethylene glycol, triethylene glycol, tetraethylene glycol, dipropylene glycol, and other alkylene glycols in which the alkylene radical contains from 2 to 8 carbon atoms. Other useful polyhydric alcohols include glycerol, mono-oleate of glycerol, monostearate of glycerol, monomethyl ether of glycerol, pentaerythritol, dipentaerythritol, etc.

The ester dispersant may also be derived from unsaturated alcohols such as allyl alcohol, cinnamyl alcohol, propargyl alcohol, 1-cyclohexane-3-ol, and oleyl alcohol. Still other classes of alcohols capable of yielding the esters comprise the ether-alcohols and amino-alcohols including, for example the oxy-alkylene-, oxy-arylene-, amino-alkylene-, and amino-arylene-substituted alcohols having one or more oxy-alkylene, amino-alkylene or amino-arylene or amino-arylene oxy-arylene radicals. They are exemplified by Cellosolve, carbitol, N,N,N',N'-tetrahydroxy-tri-methylene di-amine, and ether-alcohols having up to about 150 oxyalkylene radicals in which each alkylene radical contains from 1 to 8 carbon atoms.

The ester dispersant may be a di-ester of succinic acid or an acidic ester (i.e. a partially esterified succinic acid), or a partially esterified polyhydric alcohol or phenol, (i.e. an ester having free alcoholic or phenolic hydroxyl radicals). Mixtures of the above illustrated esters are likewise contemplated.

The ester dispersant may be prepared by one of several known methods as illustrated for example in U.S. Pat. No. 3,381,022, hereby incorporated by reference in their entirety.

Mannich base type dispersants such as those described in U.S. Pat. Nos. 3,649,229 and 3,798,165 (hereby incorporated by reference in their entirety) may also be used in these compositions. Such Mannich base dispersants can be formed by reacting a high molecular weight, hydrocarbyl-substituted mono- or polyhydroxylbenzene (e.g. having a number average molecular weight of 1,000 or greater) with amines (e.g. polyalkyl polyamines, polyalkenyl polyamines, aromatic amines, carboxylic acid-substituted polyamines and the succinimide formed from any one of these with an olefinic succinic acid or anhydride) and carbonyl compounds (e.g. formaldehyde or para formaldehyde).

A particularly suitable dispersant is one derived from polyisobutylene substituted with succinic anhydride groups and reacted with polyethylene amines, e.g. tetraethylene pentamine, pentaethylene hexamine, polyoxyethylene and polyoxypropylene amines, e.g. polyoxypropylene diamine, trismethylolaminomethane and pentaerythritol, and combinations thereof Detergents Metal-containing rust inhibitors and/or detergents are frequently used with ashless dispersants. Such detergents and rust inhibitors include oil-soluble mono- and dicarboxylic acids, the metal salts of sulfonic acids, alkyl phenols, sulfurized alkyl phenols, alkyl salicylates and naphthenates in neutral or basic form. Highly basic (or "over-based") metal salts, which are frequently used as detergents, appear particularly prone to promote oxidation of hydrocarbon oils containing them. Usually these metal-containing rust inhibitors and detergents are used in lubricating oil in amounts of from 0.01 to 10 weight percent, more preferably from 0.1 to 5 weight percent, based on the weight of the total lubricating composition.

Highly basic alkali metal and alkaline earth metal sulfonates are frequently used as detergents. They are usually produced by heating a mixture comprising an oil-soluble sulfonate or alkaryl sulfonic acid, with an excess of alkali metal or alkaline earth metal compound above that required for complete neutralization of any sulfonic acid present and thereafter forming a dispersed carbonate complex by reacting the excess metal with carbon dioxide to provide the desired overbasing. The sulfonic acids are typically obtained by the sulfonation of alkyl substituted aromatic hydrocarbons such as those obtained from the fractionation of petroleum by distillation and/or extraction or by the alkylation of aromatic hydrocarbons as for example those obtained by alkylating benzene, toluene, xylene, naphthalene, diphenyl and the halogen derivatives such as chlorobenzene, chlorotoluene and chloronaphthalene. The alkylation may be carried out in the presence of a catalyst with alkylating agents having from about 3 to more than 30 carbon atoms. For example, haloparaffins, olefins obtained by dehydrogenation of paraffins, polyolefin polymers produced from ethylene, propylene, etc. are all suitable. The alkaryl sulfonates usually contain from 9 to 70 or more carbon atoms, preferably from 16 to 50 carbon atoms per alkyl substituted aromatic moiety.

The alkali metal or alkaline earth metal compounds which may be used in neutralizing these alkaryl sulfonic acids to provide the sulfonates include the oxides and hydroxides, alkoxides, carbonates, carboxylates, sulfides, hydrosulfides, nitrates, borates and ethers of sodium, magnesium, calcium, strontium and barium. Non-limiting examples include calcium oxide, calcium hydroxide, magnesium oxide, magnesium acetate, and magnesium borate. As noted, the alkaline earth metal compound is used in excess of that required to complete neutralization of the alkaryl sulfonic acids. Generally, the amount ranges from 100 to 220 percent, although it is preferred to use at least 125 percent of the stoichiometric amount of metal required for complete neutralization.

Various other preparations of basic alkali metal and alkaline earth metal alkaryl sulfonates are known, such as those described in U.S. Pat. Nos. 3,150,088 and 3,150,089 (hereby incorporated by reference in their entirety) wherein overbasing is accomplished by hydrolysis of an alkoxide-carbonate complex with the alkaryl sulfonate in a hydrocarbon solvent-diluent oil.

Preferred alkaline earth sulfonate additives are magnesium alkyl aromatic sulfonate additives having a high total base number (TBN) as measured by ASTM 02896 of at least 250, more preferably ranging from 300 to 400, and calcium alkyl aromatic sulfonates having a TBN of at least 250, preferably from 300-400.

Neutral metal sulfonates are frequently used as rust inhibitors. Polyvalent metal alkyl salicylate and naphthenate materials are known additives for lubricating oil compositions to improve their high temperature performance and to counteract deposition of carbonaceous matter on pistons (e.g. U.S. Pat. No. 2,744,069, hereby incorporated by reference in their entirety). An increase in reserve basicity of the polyvalent metal alkyl salicylates and naphthenates can be realized by utilizing alkaline earth metal, e.g. calcium, salts of mixtures of $C_8$-$C_{26}$ alkyl salicylates and phenates (e.g. U.S. Pat. No. 2,744,069, hereby incorporated by reference in their entirety) or polyvalent metal salts of alkyl salicylic acids, said acids obtained from the alkylation of phenols followed by phenation, carboxylation and hydrolysis (e.g. U.S. Pat. No. 3,704,315, hereby incorporated by reference in their entirety) which could then be converted into highly basic salts by techniques generally known and used for such conversion. The reserve basicity of these metal-containing rust inhibitors is useful at TBN levels of between 60 and 150. Non-limiting examples of useful polyvalent metal salicylate and naphthenate materials are the methylene and sulfur bridged materials which are readily derived from alkyl substituted salicylic or naphthenic acids or mixtures of either or both with alkyl substituted phenols. Basic sulfurized salicylates and a method for their preparation are disclosed in U.S. Pat. No. 3,595,791, hereby incorporated by reference in their entirety. Such materials include alkaline earth metal, particularly magnesium, calcium, strontium and barium, salts of aromatic acids having the general formula:

HOOC—ArR$^{31}$OH-Q$_k$(ArR$^{31}$OH)$r$ where Ar is an aryl radical of 1 to 6 rings, R31 is an alkyl group having from 8 to 50 carbon atoms, preferably 12 to 30 carbon atoms (optimally about 12), Q is a sulfur (—S—) or methylene (—CH$_2$—) bridge, k is a number from 0 to 4 and r is a number from 0 to 4.

Preparation of the overbased methylene bridged salicylate-phenate salt is readily carried out by conventional techniques such as by alkylation of a phenol followed by phenation, carboxylation, hydrolysis, methylene bridging a coupling agent such as an alkylene dihalide followed by salt formation concurrent with carbonation. An overbased calcium salt of a methylene bridged phenol-salicylic acid with a TBN of 60 to 150 is also useful.

Another type of basic metal detergent, the sulfurized metal phenates, can be considered a metal salt whether neutral or basic, of a compound typified by the general formula:

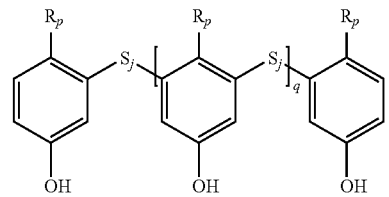

where j=1 or 2, q=0, 1 or 2 or a polymeric form of such a compound, where Rp is an alkyl radical, j and q are each integers from 1 to 4, and the average number of carbon atoms in all of the R groups is at least about 9 in order to ensure adequate solubility in oil. The individual Rp groups may each contain from 5 to 40, preferably 8 to 20, carbon atoms. The metal salt is prepared by reacting an alkyl phenol sulfide with a sufficient quantity of metal containing material to impart the desired alkalinity to the sulfurized metal phenate.

Regardless of the manner in which they are prepared, the sulfurized alkyl phenols which are useful generally contain from 2 to 14 percent by weight, preferably 4 to 12 weight percent sulfur based on the weight of sulfurized alkyl phenol. The sulfurized alkyl phenol may be converted by reaction with a metal-containing material including oxides, hydroxides and complexes in an amount sufficient to neutralize said phenol and, if desired, to overbase the product to a desired alkalinity by procedures well known in the art. Preferred is a process of neutralization utilizing a solution of metal in glycol ether.

The neutral or normal sulfurized metal phenates are those in which the ratio of metal to phenol nucleus is about 1:2. The "overbased" or "basic" sulfurized metal phenates are sulfurized metal phenates wherein the ratio of metal to phenol is greater than the stoichiometric ratio, e.g. basic sulfurized metal dodecyl phenate has a metal content up to (or greater) than 100 percent in excess of the metal present in the corresponding normal sulfurized metal phenate. The excess metal is produced in oil-soluble or dispersible form (as by reaction with $CO_2$).

The detergents which may be included in the compositions of the present invention may optionally be borated in a known manner. Such boration provides the detergent with a measure of anti-wear activity.

It is preferred to use a combination of metal-containing detergents comprising calcium and magnesium salts or calcium, magnesium and sodium salts, as described above.

Antiwear Additives (Including Extreme Pressure Agents)

A wide variety of anti-wear additives may be included in the compositions or concentrates of the invention. For example, organic sulfides and polysulfides including especially dialkyl sulfides and polysulfides (e.g. dibutyl polysulfides, and dibenzyl sulfides and polysulfides) which may be substituted (e.g. with halogen, may be incorporated in the compositions or concentrates). Sulfurized esters, (e.g. sulfurized methyl or isopropyl oleate) and other sulfurized compounds, (e.g. sulfurized olefins such as sulfurized diisobutylene, sulfurized tripropylene or sulfurized dipentene) may also be added to the compositions. More complex sulfurized compounds such as sulfurized alkyl phenols and sulfurized terpenes and Diels-Alder adducts and sulfurized polymers, e.g. butadiene/butyl acrylate copolymers, may also be used, as may sulfurized tall oil fatty acid esters. Esters of beta-thiodipropionic acid, e.g. butyl, nonyl, tridecyl or eicosyl esters may also be used.

Anti-wear additives in the form of phosphorus esters, (e.g. di- and tri-alkyl, cycloalkyl or aryl phosphites) may also be used. Examples of such phosphites include dibutyl phosphite, dihexyl phosphite, dicyclohexyl phosphite, alkyl phenyl phosphites such as dimethylphenyl phosphite and mixed higher alkyl, (e.g. oleyl, alkyl phenyl phosphate, an example of which includes 4-pentyl phenyl phosphite). Phosphites based on polymers such as low molecular weight, polyethylenes and polypropylenes may also be used.

Preferred anti-wear additives for addition to the compositions and concentrates of the present invention are the dihydrocarbyl dithiophosphate metal salts. They also provide some antioxidant activity. The zinc salts are most commonly used in lubricating oils in amounts of 0.1 to 10, preferably 0.2 to 2, weight percent, based upon the total weight of the lubricating oil composition. Salts of other metals, e.g. barium and cadmium, can also be used. They may be prepared in accordance by first forming a dithiophosphoric acid, usually by reaction of an alcohol or a phenol with P2 S5 and then neutralizing the dithiophosphoric acid with a suitable zinc compound.

Alcohols may be used including mixtures of primary and secondary alcohols, with secondary alcohol generally for imparting improved antiwear properties, and primary alcohols forgiving improved thermal stability properties. Mixtures of the two are particularly useful. In general, any basic or neutral zinc compound could be used but the oxides, hydroxides and carbonates are most generally employed. Commercial additives frequently contain an excess of zinc due to use of an excess of the basic zinc compound in the neutralization reaction.

The zinc dihydrocarbyl dithiophosphates useful in the present invention are oil-soluble salts of dihydrocarbyl esters of dithiphosphoric acids and may be represented by the following formula

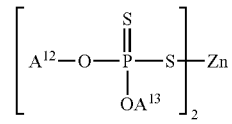

wherein $A^{12}$ and $A^{13}$ may be the same or different hydrocarbyl radicals containing from 1 to 18, preferably 2 to 12, carbon atoms and including radicals such as alkyl, alkenyl, aryl, aralkyl, alkaryl and cycloaliphatic radicals. Particularly preferred as $A^{12}$ and $A^{13}$ groups are alkyl groups of 2 to 8 carbon atoms. Thus, the radicals may, for example be ethyl, n-propyl, i-propyl, n-butyl, i-butyl, sec-butyl, amyl, s-hexyl, i-hexyl, i-octyl, decyl, dodecyl, octadecyl, 2-ethylhexyl, nonyl-phenyl, dodecyl-cyclohexyl, methylcyclopentyl, propenyl, butenyl, etc. In order to obtain oil solubility, the total number of carbon atoms in the dithiophosphoric acid (i.e. $A^{12}$ and $A^{13}$) generally should be about 5 or greater and preferably 8 or greater.

Borated derivatives of the aforesaid antiwear agents may also be included in the compositions or concentrates of the invention.

Thiadiazole

The 1,3,4-thiadiazoles of formula I may be prepared by the method disclosed in U.S. Pat. Nos. 4,761,482 and 4,880,437, incorporated herein by reference in their entirety:

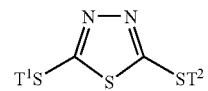

wherein $T^1$ and $T^2$ are independently selected from the group consisting of hydrogen, alkyl, hydroxyalkyl, alkylthio, phenylalkyl, alkylated phenylalkyl, terpene residue and maleic acid residue of the formula

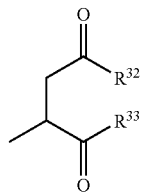

wherein $R^{32}$ and $R^{33}$ are independently selected from the group consisting of hydrogen, branched or straight chain alkyl groups and cyclic aliphatic groups, wherein at least one of $R^{32}$ and $R^{33}$ is not hydrogen.

An embodiment for the present invention includes alkyls which have from 1 to 50 carbon atoms which may be branched or straight chain and may be substituted with a hydroxyl group and an aryl group. Another embodiment for the present invention are $T^1$ and $T^2$ which are alkyl and alkylthio groups which contain 1 to 22 carbon atoms and may be branched or straight chain. Additional embodiments for the present invention include compounds wherein $T^1$ and $T^2$ together contain a total of at least 22 carbon atoms in their alkyl and/or alkylthio groups.

Embodiments of terpene residues for the present invention include terpenes which are derived from pinene and limonene.

An embodiment of maleic acid residues for the present invention include maleic acid residues where $R^{32}$ and $R^{33}$ independently represents an alkyl group with 1 to 22 carbon atoms or C5-C7 cycloalkyl group. A further embodiment includes the total number of carbon atoms for $R^{32}$ and $R^{33}$ combined being from 8 to 44 carbon atoms.

Commercially available thiadiazoles derivatives are VAN-LUBE® 871 (butanedioic acid ((4,5-dihydro-5-thioxo-1,3,4-thiadiazol-2-yl)thio-bis(2-ethylhexyl)ester) CUVAN® 826 (2,5-dimercapto-1,3,4-thiadiazole) and CUVAN® 484 (alkylthiadiazole) manufactured by R. T. Vanderbilt Company, Hitec™ 4313, 4312, RC 8210, and RC 8213.

Dithiocarbamates (i) Bisdithiocarbamates

The bisdithiocarbamates of formula are known compounds described in U.S. Pat. No. 4,648,985, incorporated herein by reference in its entirety.

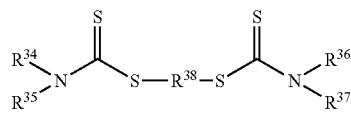

The compounds are characterized by $R^{34}$, $R^{35}$, $R^{36}$ and $R^{37}$ which are the same or different and are hydrocarbyl groups having 1 to 13 carbon atoms.

Embodiments for the present invention include bisdithiocarbamates wherein $R^{34}$, $R^{35}$, $R^{36}$ and $R^{37}$ are the same or different and are branched or straight chain alkyl groups having 1 to 8 carbon atoms.

$R^{38}$ is an aliphatic group such as straight and branched alkylene groups containing 1 to 8 carbons. An embodiment for $R^{38}$ is methylenebis(dibutyldithiocarbamate) available commercially from R. T. Vanderbilt Company, Inc. under the tradename VANLUBE® 7723, and from King Industries under the tradename NA-LUBE® ADTC.

(ii) Ashless Dithiocarbamate Esters

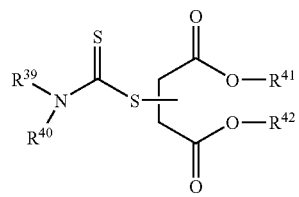

The compounds of the above formula are characterized by groups $R^{39}$, $R^{40}$, $R^{41}$ and $R^{42}$ which are the same or different and are hydrocarbyl groups having 1 to 13 carbon atoms. VANLUBE® 732 and VANLUBE® 981 are commercially available from R. T. Vanderbilt Company, Inc.

(iii) Metal Dithiocarbamates

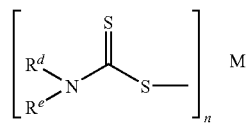

The dithiocarbamates of the above formula are known compounds. One of the processes of preparation is disclosed in U.S. Pat. No. 2,492,314, which is hereby incorporated by reference in its entirety. Rd and Re represent branched or straight chain alkyl groups having 1 to 8 carbon atoms, M is a metal cation and n is an integer based upon the valency of the metal cation (e.g. n=1 for sodium ($Na^+$); n=2 for zinc ($Zn^{++}$); etc.). Molybdenum dithiocarbamate processes are described in U.S. Pat. Nos. 3,356,702; 4,098,705; and 5,627,146, each of which is hereby incorporated by reference. Substitution is described as branched or straight chain ranging from 8 to 13 carbon atoms in each alkyl group.

Embodiments for the present invention include metal dithiocarbamates which are antimony, zinc and tungsten dithiocarbamates.

Additionally the lubricant composition may also include phosphorous dithiophosphate compounds. Embodiments of dithiophosphates for the present invention include:

(i) Metal Phosphorodithioates

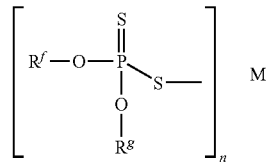

The metal phosphorodithioates are known, commercially available materials. One of the processes of preparation is taught by U.S. Pat. No. 4,215,067, which is hereby incorporated by reference in its entirety. (M and n are as defined above for the metal dithiocarbamates) $R^f$ and $R^g$ represent branched and straight chain alkyl groups having 1-22 groups and may be derived from fatty acids. In one embodiment the metal phosphorodithioates are zinc phosphorodithioates. The metal ion in formula V may be selected from the following groups of the Periodic Table: IIA, IIIA, VA, VIA, IB, IIB, VIB and VIII. Amine salts of the compounds are also useful synergists of the invention. Embodiments of such amine salts include those prepared from alkyl amines and mixed alkyl amines. An additional embodiment includes amine salts based on fatty acid amines.

(ii) Phosphorodithioate esters

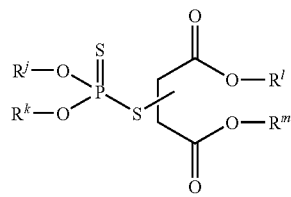

The phosphorodithioate esters are known compounds. One of the processes of manufacture is disclosed in U.S. Pat. No.

3,567,638, which is hereby incorporated by reference in its entirety. $R^j$, $R^k$, $R^l$ and $R^m$ may be the same or different and may be branched and straight chain alkyl groups. Embodiments for the present invention include branched or straight chain alkyl groups containing 1 to 8 carbon atoms.

Embodiments for the ranges of phosphorodithioate (also known as dithiophosphate) compound, or mixture of dithiophosphate compounds, are 0.05-2.00%; 0.5-1.50%; and 0.5-0.8% (each percentage being percent by weight based upon the total weight of the composition).

Additional Antioxidants

Additional antioxidants which are especially useful in lubricating oil compositions or concentrates are based on oil-soluble copper compounds, e.g. in the form of a synthetic or natural carboxylic acid salt. By "oil-soluble" is meant that the compound is oil-soluble or solubilized under normal blending conditions in the oil or concentrate. Examples of oil-soluble copper compounds include salts of $C_{10}$ to $C_{18}$ fatty acids such as stearic or palmitic acid; but unsaturated acids (such as oleic acid), branched carboxylic acids (such as naphthenic acids) of molecular weight from 200 to 500, dicarboxylic acids such as polyisobutenyl succinic acids, and synthetic carboxylic acids can all be used because of the acceptable handling and solubility properties of the resulting copper carboxylates.

Suitable oil-soluble copper dithiocarbamates have the general formula

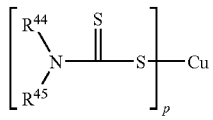

where p is 1 or 2 and R44 and R45 may be the same or different hydrocarbyl radicals containing from 1 to 18 carbon atoms each and including radicals such as alkyl, alkenyl, aryl, aralkyl, alkaryl and cycloaliphatic radicals. Particularly preferred as $R^{44}$ and $R^{45}$ groups are alkyl groups of 2 to 8 carbon atoms. Thus, the radicals may be, for example, ethyl, n-propyl, n-butyl, i-butyl, sec-butyl, amyl, sec-hexyl, i-hexyl, i-octyl, decyl, dodecyl, octadecyl, 2-ethylhexyl, nonyl-phenyl, dodecyl-phenyl, cyclohexyl, methylcyclopentyl, propenyl, butenyl, etc. In order to obtain oil solubility, the total number of carbon atoms (i.e. $R^{44}$ and $R^{45}$) generally should be about 5 or greater.

Copper salts of dithiophosphonic acids (the acid as described hereinbefore in relation to antiwear additives specifically as zinc salts), copper sulfonates, phenates, copper polyisobutylene succinic anhydride ("Copper PIBSA") carboxylates such as oleates, stearates and mixtures thereof, and acetyl acetonates can also be used.

These antioxidants can be used in amounts such that, in the final lubricating composition, a copper concentration of from 5 to 500 ppm is present.

Other known oil-soluble or oil-ispersible, and preferably liquid, antioxidants may also be used in the compositions of the invention. Examples of such antioxidants include hindered phenols, which may contain sulphur, e.g. 4,4'-methylene bis(2,6-di(t-butyl)phenol), 4,4'-thio bis(2,6-di(t-butyl) phenol) and p-alkylated hindered phenols; unhindered phenols which again may contain sulphur such as 2,2'-thio bis-(4-nonyl phenol) and 2,2'-methylene bis(4-nonylphenol); phenothiazine derivatives, e.g. those containing higher alkyl substituents such as dioctyl and dinonyl phenothiazines; substituted alpha and betanaphthyl amines such as phenyl beta-naphthylamine and its alkylated derivatives; other amino aryl compounds such as for example 4,4'-bis(secbutylamino) diphenylmethane; dithiocarbamates such as zinc, nickel, copper, or molybdenum dithiocarbamates; and phosphosulfurized olefins, e.g. phosphosulfurized pinene or styrene.

Corrosion Inhibitors and Metal Deactivators

Corrosion inhibitors which act by deactivating metal parts with which they come in contact and/or as sulfur scavengers can also be used in the compositions or concentrates of the invention. Examples of such agents include benzotriazole derivatives; thiadiazole compounds, e.g. 2,5-dimercapto 1,3, 4-thiadiazole; mercaptobenzothiazole compounds in the form of amine salts, sulphonamides, thiosulphonamides, and condensates of mercaptobenzothiazole with amines and formaldehyde; salicylaldehyde/diamine condensation products; dialkylphosphites, e.g. dioleyl or di-2-ethylhexyl phosphite; trialkyl and triarylphosphites, e.g. tris-(2-ethyl-hexyl), triphenyl or tri(4-nonylphenol) phosphites; and thiophosphonates such as triphenyl or trilauryl thiophosphonate or trilauryl tetrathiophosphonate.

Also useful are corrosion inhibitors based on aromatic sulfonic acid derivatives, for example derivative of a mono-, di-, or poly-alkylated naphthalenesulfonic acid selected from the group consisting of:

(i) neutral metal salts of said mono-, di-, and poly-alkylated naphthalenesulfonic acids;

(ii) basic metal salts of said mono-, di-, and poly-alkylated naphthalenesulfonic acids;

(iii) amine salts of said mono-, di-, and poly-alkylated naphthalenesulfonic acids; and (iv) esters of said mono-, di-, and poly-alkylated naphthalenesulfonic acids; wherein the mono-, di-, and poly-alkylated naphthalenesulfonic acids are represented by formula

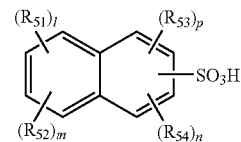

wherein $R_{51}$, $R_{52}$, $R_{53}$ and $R_{54}$ are individually selected from the group consisting of hydrogen or essentially linear hydrocarbyl groups having about 9 to about 22 carbon atoms; and wherein l, m, n and p are integers from 0 to 4 and the sum of l+m+n+p is at least 1; and wherein $R_{51}$, $R_{52}$, $R_{53}$ and $R_{54}$ is a hydrogen where either l, m, n, or p is 0.

One derivative of the alkylated naphthalenesulfonic acid composition is the neutral metal salt component and is represented by the formula (II):

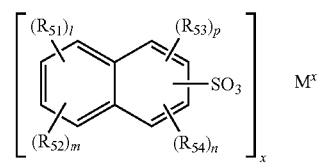

wherein $R_{51}$, $R_{52}$, $R_{53}$ and $R_{54}$, l, m, n and p are as defined above; M is a metal selected from the group consisting of alkali metals, alkaline earth metals, transition metals, Group IVb metals, and Group Vb metals; and x is the valence of M.

M in formula (II) is an alkali metal selected from the group consisting of lithium, sodium, potassium, and mixtures thereof. M may also be an alkaline earth metal selected from the group consisting of magnesium, calcium, strontium, barium and mixtures thereof. In other embodiments, M is a transition metal selected from the group consisting of zinc, copper, cerium, molybdenum, and mixtures thereof. In still other embodiments M may be a Group IVb metal and selected from the group consisting of tin, lead, and mixtures thereof. M may be a Group Vb metal selected from the group consisting of bismuth, antimony, and mixtures thereof.

The functional fluid composition may also contain at least one derivative of the alkylated naphthalenesulfonic acid composition that is the overbased metal salt component described above and represented by forulae

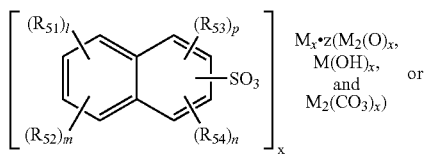

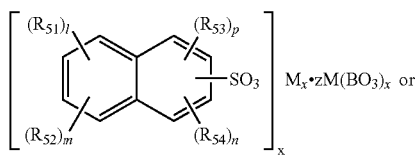

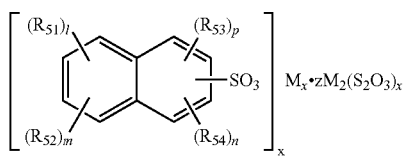

and mixtures thereof wherein $R_{51}$, $R_{52}$, $R_{53}$ and $R_{54}$, l, m, n and p are as defined earlier; M is a metal selected from the group consisting of alkali metals, alkaline earth metals, transition metals, Group IVb metals, and Group Vb metals; x is the valence of M; and z is 0.1 to 50.

The functional fluid composition contains one ammonium or organic amine salt of formulae

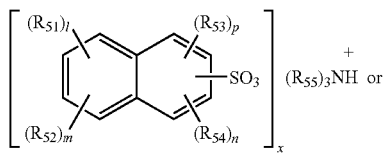

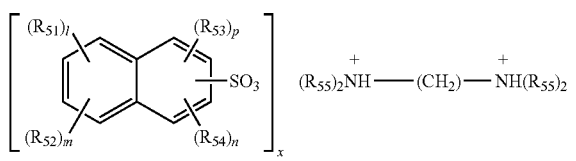

wherein $R_{51}$, $R_{52}$, $R_{53}$ and $R_{54}$, l, m, n and p are as defined earlier and each $R_{55}$ is individually selected from a hydrogen atom or a hydrocarbyl group consisting of from 1 to 25 carbon atoms; and x is from 2 to 5.

The functional fluid composition contains at least one compound represented by formula

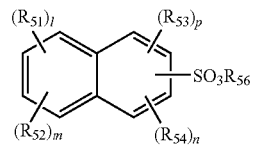

wherein $R_{51}$, $R_{52}$, $R_{53}$ and $R_{54}$, l, m, n and p are as defined earlier and $R_{56}$ is a hydrocarbyl group consisting of from 2 to 18 carbon atoms.

Also useful are corrosion inhibitors based on N-acyl-N-hydrocarbonoxyalkyl aspartic acid compounds having the formula

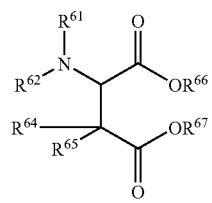

wherein $R^{61}$ is a hydrocarbonoxyalkyl group of from about 6 to about 30 carbon atoms, $R^{62}$ is a carboxyl substituted acyl group containing from about 2 to about 30 carbon atoms, or such a group at least partially neutralized with an alkali metal base, an alkaline earth metal base, an amine or a mixture of any of the foregoing, and $R^{64}$, $R^{65}$, $R^{66}$, and $R^{67}$ are each, independently, selected from hydrogen or a hydrocarbon group of from about 1 to about 30 carbon atoms.

Friction Modifiers and Fuel Economy Agents

Friction modifiers and fuel economy agents, compatible with the other ingredients of the new compositions or concentrates may also be included. Examples of such materials are glyceryl monoesters and/or diesters of higher fatty acids, e.g. glyceryl mono-oleate and esters of long-chain polycarboxylic acids with diols, e.g. the butane diol ester of a dimerized unsaturated fatty acid, and oxazoline compounds.

Succinimides

Succinimides friction modifiers of the current invention may be represented by the following general formula.

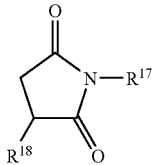

where R18 is a C6 to C30 isomerized alkenyl group, represented by:

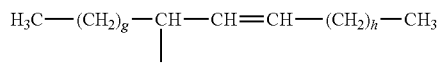

(where g and h are integers whose sum is from 1 to 25), or its fully saturated alkyl analog, R17 is an alkyl group, aryl group, and their heteroatom containing derivatives.

The succinimides of the present invention are those produced from succinic anhydrides substituted with isomerized alkenyl groups or their fully saturated alkyl analogs. Preparation of the isomerized alkenyl succinic anhydrides is described in, for example, U.S. Pat. No. 3,382,172 hereby incorporated by reference in its entirety.

Often these materials are prepared by heating alpha-olefins with acidic catalysts to migrate the double bond to form an internalolefin. This mixture of olefins (2-enes, 3-enes, etc.) is then thermally reacted with maleic anhydride. Typically olefins from $C_6$ (e.g. 1-hexene) to $C_{30}$ (e.g. 1-tricosane) are used. Suitable isomerized alkenyl succinic anhydrides of structure (1)

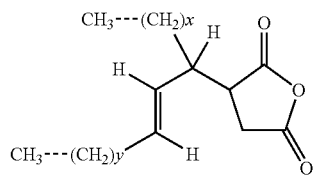

include isodecylsuccinic anhydride (x+y=5), iso-dodecyisuccinic anhydride (x+y=), iso-tetradecylsuccinic anhydride (x+y=9), iso-hexadecylsuccinic anhydride (x+y=1), iso-octadecylsuccinic anhydride (x+y=13) and isoeicosylsuccinic anhydride (x+y=15). Preferred materials are isohexadecylsuccinic anhydride and iso-octadecylsuccinic anhydride.

The materials produced by this process contain one double bond (alkenyl group) in the alkyl chain. The alkenyl substituted succinic anhydrides may be easily converted to their saturated alkyl analogs by hydrogenation.

Suitable primary and secondary amines useful to produce the succinimides are represented by structure

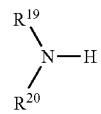

where: $R^{19}$ and $R^{20}$ are independently alkyl, aryl, their heteroatom containing derivatives, or H with the proviso that $R^{19}$ and $R^{20}$ are not both H. Preferred amines are n-hexylamine, di-n-hexylamine, dimethylamine, n-butylamine, diethanol amine and di-methylaminopropylamine.

Bis succinimides of the current invention may be represented by the following general formula

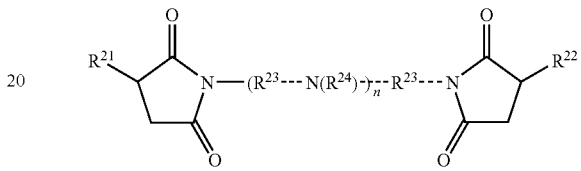

wherein $R^{21}$ and $R^{22}$ may be identical or different from each other and are each hydrocarbon groups having 5 or more carbons; $R^{23}$ is a divalent hydrocarbon group having 1 to 5 carbons; $R^{24}$ is a hydrogen atom or a hydrocarbon group having 1 to 20 carbons; and n is an integer in the range of 0 to 10

In the above general formula, $R^{21}$ and $R^{22}$ may be the same as each other or different from each other, and are each saturated or unsaturated hydrocarbon groups having 5 or more carbons, preferably 5 to 40 carbons. Examples of hydrocarbon groups include pentyl groups, hexyl groups, heptyl groups, octyl groups, nonyl groups, decyl groups, dodecyl groups, tridecyl groups, tetradecyl groups, pentadecyl groups, hexadecyl groups, heptadecyl groups, octadecyl groups, nonadecyl groups, oleyl groups and other hydrocarbon groups having up to 40 carbons. Preferred hydrocarbon groups include straight chain hydrocarbon groups having between 8 and 25 carbons. In the above general formula, $R^{23}$ is a divalent hydrocarbon group having 1 to 5 carbons, preferably an alkylene group having 2 or 3 carbons.

In the above general formula, $R^{24}$ is a hydrogen atom or a hydrocarbon group having 1 to 20 carbons. Examples of hydrocarbon groups include alkyl groups having 1 to 20 carbons; alkenyl groups having 2 to 20 carbons; cycloalkyl groups having 6 to 20 carbons; and aryl groups having 6 to 20 carbons. The aryl groups may have an alkyl group having 1 to 12 carbons. Hydrogen atoms and alkyl groups having 1 to 10 carbons are particularly preferred as $R^{24}$. Groups having a number of amino groups and/or amide bonds in their structure (e.g. 1 to 5 of each) can be used as the above-described hydrocarbon groups.

The amino groups are represented by —NH— or —NH$_2$; and the amide bonds are represented by

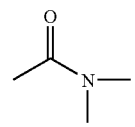

They may be bonded with the carbons of the hydrocarbon group at an arbitrary position.

The bis succinimides of the present invention are those produced from succinic anhydrides substituted with isomerized alkenyl groups or their fully saturated alkyl analogs, and polyamines. Suitable polyamines are saturated amines of the general formula

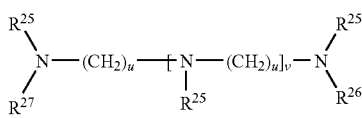

where $R^{25}$, $R^{26}$, and $R^{27}$ are independently selected from the group consisting of H, $C_1$ to $C_{25}$ straight or branched chain alkyl radicals, $C_1$ to $C_{12}$ alkoxy radicals; $C_2$ to $C_6$ alkylene radicals; u is an integer from 1 to 6, preferably 2 to 4; and v is an integer from 0 to 10, preferably from 1 to 4.

Non-limiting examples of suitable polyamine compounds include: 1,6-diaminohexane, diethylene triamine, triethylene tetramine, tetraethylene pentamine, and pentaethylene hexamine. Useful mixtures of polyamines having from 5 to 7 nitrogen atoms per molecule are available from Dow Chemical Co. as Polyamine H, Polyamine 400 and Polyamine E-300.

Polyoxyalkylene amines are also useful in this invention and are shown as structure

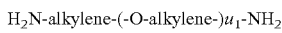

where $u_1$ is an integer of from 1 to 10. The polyamines have molecular weights from about 100 to 500. The preferred polyoxyalkylene polyamines include polyoxyethylene and polyoxypropylene diamines and the polyoxypropylene triamines. Commercial polyoxyalkylene amines are available from Jefferson Chemical Co. sold under the trade name "Jeffamines® D-230, D-400, D-1 000, T-430," etc.

In preferred embodiments, the alkenyl succinic anhydride starting materials for forming the friction modifiers of above structure can be either of two types. The two types differ in the linkage of the alkyl side chain to the succinic acid moiety. In the first type, the alkyl group is joined through a primary carbon atom in the starting olefin, and therefore the carbon atom adjacent to the succinic acid moiety is a secondary carbon atom. In the second type, the linkage is made through a secondary carbon atom in the starting olefin and these materials accordingly have a branched or isomerized side chain. The carbon atom adjacent to the succinic acid moiety therefore is necessarily a tertiary carbon atom.

The alkenyl succinic anhydrides of the first type, shown below, with linkages through secondary carbon atoms, are prepared simply by heating α-olefins, that is, terminally unsaturated olefins, with maleic anhydride. Non-limiting examples of these materials include n-decenyl succinic anhydride, tetradecenyl succinic anhydride, n-octadecenyl succinic anhydride, tetrapropenyl succinic anhydride, poly butenyl succinic anhydrides, etc.

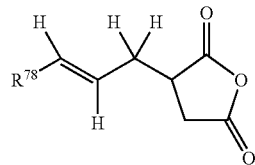

wherein $R^{78}$ is $C_2$ to $C_{37}$ alkyl.

A second type of alkenyl succinic anhydrides, with linkage through tertiary carbon atoms, is produced from internally unsaturated olefins and maleic anhydride. Internal olefins are olefins which are not terminally unsaturated, and therefore do not contain the

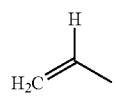

moiety. These internal olefins can be introduced into the reaction mixture as such, or they can be produced in situ by exposing α-olefins to isomerization catalysts at high temperatures. A process for producing such materials is described in U.S. Pat. No. 3,382,172 hereby incorporated by reference in its entirety. The isomerized alkenyl substituted succinic anhydrides are compounds having structure

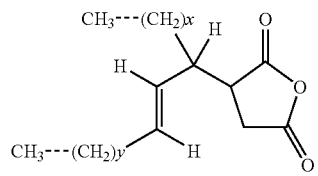

where x and y are independent integers whose sum is from 1 to 35.

The preferred succinic anhydrides are produced from isomerization of linear α-olefins with an acidic catalyst followed by reaction with maleic anhydride. The preferred α-olefins are 1-octene, 1-decene, 1-dodecene, 1-tetradecene, 1-hexadecene, 1-octadecene, 1-eicosane, or mixtures of these materials. The products described can also be produced from internal olefins of the same carbon numbers, 8 to 20. The preferred materials for this invention are those made from 1-tetradecene (x+y=9), 1-hexadecene (x+y=11), 1-octadecene (x+y=13), 1-didodecene (x+y=15), and 1-tetradidodecene (x+y=19) or mixtures thereof.

The preferred succinimide friction modifiers of this invention are products produced by the reaction of isomerized alkenyl succinic anhydride with diethylene triamine, triethylene tetramine, tetraethylene pentamine or mixtures thereof. The most preferred products are prepared using diethylene triamine, triethylene tetramine, and tetraethylene pentamine. The alkenyl succinic anhydrides are typically reacted with the amines in a 2:1 molar ratio so that both primary amines are converted to succinimides. Sometimes a slight excess of isomerized alkenyl succinic anhydride is used to insure that all primary amines have reacted.

The two types of succinimide friction modifiers can be used individually or in combination.

The disuccinimides may be post-treated or further processed by any number of techniques known in the art. These techniques would include, but are not limited to, boration, maleation, and acid treating with inorganic acids such as phosphoric acid, phosphorous acid, and sulfuric acid. Descriptions of these processes can be found in, for example, U.S. Pat. Nos. 3,254,025; 3,502,677; 4,686,054; and 4,857,214 hereby incorporated by reference in their entirety.

Other useful derivatives of the succinimide modifiers are where the alkenyl groups of above structures have been hydrogenated to form their saturated alkyl analogs. Saturation of the condensation products of olefins and maleic anhydride may be accomplished before or after reaction with the amine. These saturated versions of above structures may likewise be post-treated as previously described.

While any effective amount of the compounds of above structure and its derivatives may be used to achieve the benefits of this invention, typically these effective amounts will range from 0.01 to 10 weight percent of the finished fluid, preferably from 0.05 to 7 weight percent, most preferably from 0.1 to 5 weight percent.

Viscosity Index Improvers

Viscosity index improvers or viscosity modifiers are typically polymers of number average molecular weight 103 to 106—for example ethylene copolymers or polybutenes. Viscosity index improvers may be modified to have dispersant properties and suitable viscosity index improver dispersants for use in compositions of the invention are described in, for example, EP 24 146 A and are as follows:

(a) polymers comprising monomer units derived from a $C_4$ to $C_{24}$ unsaturated ester of vinyl alcohol or a $C_3$ to $C_{10}$ unsaturated mono- or dicarboxylic acid and an unsaturated nitrogen-containing monomer having 4 to 20 carbon atoms;

(b) polymers comprising monomer units derived from a $C_4$ to $C_{20}$ olefin and an unsaturated $C_3$ to $C_{10}$ mono- or dicarboxylic acid neutralized with an amine, a hydroxyamine or an alcohol; and (c) polymers of ethylene with a $C_3$ to $C_{20}$ olefin further reacted by grafting a $C_4$ to $C_{20}$ nitrogen-containing monomer thereon or by grafting an unsaturated acid onto the polymer backbone and then reacting the carboxylic acid groups with an amine, hydroxy amine, or alcohol. (Other additives which may be used in accordance with the present invention are described in EP24146A). These viscosity index improvers also have dispersant properties, as is preferred in accordance with the invention, although viscosity index improvers without dispersant properties may be used if desired.

Preferred viscosity index improvers with dispersant properties for use in the compositions of the present invention comprise a polyolefin moiety to which is grafted an unsaturated carboxylic acid moiety, the carboxylic acid groups being reacted with an amine, hydroxyamine or alcohol.

Antioxidants may be evaluated using the sequence III E test (ASTM STP 315) which is a standard test used for assessing the oxidation resistance of lubricants and which is a more stringent version of the sequence III D test (ASTM STP 315M and ASTM STP 315). The sequence III method produces a result after 64 hrs of testing with an acceptable performance being a 375% or less increase in kinematic viscosity as measured at 40° C. after this period. The principle of this method is to observe oil thickening as a result of oxidation. When evaluating antioxidants for lubricants it is desirable to be able to use screening test methods which are quicker and easier to use than the Sequence III test. One such method which is commonly used is a thin film high temperature catalytic oxidation test performed using a DSC.

The invention will be further illustrated by means of the following examples. The following examples illustrate the invention and are not to be used to limit the scope of the invention.

Preparation of Amine Tungstates from Tungstic Acid (Method A)

A mixture of the starting amine (2 eq.), tungstic acid (1 eq.), dissolved in aqueous ammonia was stirred at 95-1100 C for 2-3 hrs, and water and excess ammonia were then removed by distillation followed by the isolation of the product as viscous liquid.

Preparation of Amine Tungstates from Ammonium Para Tungstate (Method B)

A mixture of the starting amine (26 eq.) and aqueous ammonium paratungstate (1 eq.) was heated with vigorous mixing. Water and excess ammonia were then removed by distillation followed by the isolation of the product as viscous liquid.

Preparation of Amine Tungstates from Metal Tungstates (Method C)

Tungstic acid can also be prepared from an appropriate metal tungstate and sulfuric acid. The reaction of tungstic acid (1 eq.) with the appropriate amine (2 eq.) can be conducted in a hydrocarbon solvent at elevated temperatures, to yield the desired amine tungstate product.

Preparation of Amine Tungstates from Metal Tungstates and Quaternary Ammonium Halides or Sulfates (Method D)

The amine tungstates can also be prepared by the reaction of quaternary ammonium halides or sulfates, in heptane with sodium or potassium tungstate in water.

| Example | Starting amine | Method Used | Physical Form | % W |
|---|---|---|---|---|
| 1 | Primene JMT($C_{16}$–$C_{22}$ tert-alkyl primary aliphatic amine) | A | Yellow Liquid | 18.7 |
| 2 | Primene JMT($C_{16}$–$C_{22}$ tert-alkyl primary aliphatic amine) | B | Yellow Liquid | 19.5 |
| 3 | Primene JMT($C_{16}$–$C_{22}$ tert-alkyl primary aliphatic amine) | C | Yellow Liquid | 11 |
| 4 | Primene JMT($C_{16}$–$C_{22}$ tert-alkyl primary aliphatic amine) | C (tungstic acid:amine 1:1) | Yellow Liquid | 32.6 |
| 5 | Primene JMT($C_{16}$–$C_{22}$ tert-alkyl primary aliphatic amine) | D | Yellow viscous Liquid | 34 |

-continued

| Example | Starting amine | Method Used | Physical Form | % W |
|---|---|---|---|---|
| 6 | Primene 81R(C12–C14 tert-alkyl primary aliphatic amine amine) | A | White waxy solid | 18 |
| 7 | Di(tridecyl) amine | A | Yellow liquid | 9.1 |
| 8 | Di(tridecyl) amine | B | Yellow liquid | 15.0 |
| 9 | Di(tridecyl) amine | C | Yellow liquid | 28.4 |
| 10 | Salt of N-oleyl-1,3-propanediamine (Duomeen OL), with Dinonyl naphthalene sulfonic acid | B | Blue-Green Liquid | 8.9 |
| 11 | Salt of N-oleyl-1,3-propanediamine (Duomeen OL), with Didodecyl naphthalene sulfonic acid | B | Blue-Green Liquid | 8.3 |
| 12 | Salt of N-oleyl-1,3-propanediamine (Duomeen OL), with Naphthenic acid | B | Yellow Liquid | 13.8 |
| 13 | Reaction product of Canola Oil with N-oleyl-1,3-propanediamine (Duomeen OL) | B | Yellow Liquid | 9.6 |
| 14 | Reaction product of aminoethyl imidazoline with Didodecyl naphthalene sulfonic acid | C | Yellow Liquid | 8.0 |
| 15 | Bis succinimide from alkenyl succinic anhydride and diethylene triamine | B | Yellow Liquid | 2.5 |
| 16 | Bis(2-hydroxyethyl)cocoalkylamine | B | Yellow Liquid | 17.4 |
| 17 | Alkyl (C14–C18) bis(2-hydroxyethyl) amine | B | Yellow Liquid | 5.7 |
| 18 | Alkyl (C14–C18) bis(2-hydroxyethyl) amine | B | Yellow Liquid | 7.9 |
| 19 | Salt of N-oleyl-1,3-propanediamine(Duomeen OL), with Di(2-ethylhexyl) phosphonic acid | B | Yellow Liquid | 7.4 |
| 20 | Salt of N-oleyl-1,3-propanediamine(Duomeen OL), with Di(2-ethylhexyl) dithiophosphoric acid | B | Brown Liquid | 10.9 |
| 21 | Bis succinimide from alkenyl succinic anhydride and diethylene triamine | C | Yellow Liquid | 8.3 |
| 22 | Salt of N-oleyl-1,3-propanediamine(Duomeen OL), with dioleyl phosphonic acid | B | Yellow Liquid | |

Preparation of New Amine Molybdates

A solution of starting amine (2 eq.), in heptane was combined with Molybdenum trioxide (1 eq.) in water and the resulting mixture was heated under reflux for 4-6 hrs. Water was removed by azeotropic distillation, under reduced pressure, resulting in the desired amine molybdates as a viscous oily product.

Another method involved the reaction of sodium molybdate (1 eq.) in water with amine (2 eq.) at 60-70° C., for 1 hr., followed by the addition of 1 eq., of aqueous sulfuric acid. The aqueous layer was separated and the organic residue was dehydrated under reduced pressure resulting in the desired molybdate as a viscous oily product.

Yet another method involved the reaction of ammonium molybdate (1 eq.), with amine (2 eq.) in refluxing toluene, and removing water continuously. The molybdate was isolated as a viscous liquid.

| Example | Starting amine | Moly source Used | Physical Form | % Mo |
|---|---|---|---|---|
| 23 | Salt of N-oleyl-1,3-propanediamine (Duomeen OL), with Dinonyl naphthalene sulfonic acid | MoO$_3$ | Brown Liquid | 5.37 |
| 24 | Salt of N-oleyl-1,3-propanediamine (Duomeen OL), with Naphthenic acid | MoO$_3$ | Viscous Yellow Liquid | 4.1 |
| 25 | Salt of N-oleyl-1,3-propanediamine(Duomeen OL), with Di(2-ethylhexyl) phosphoric acid | MoO$_3$ | Yellow Liquid | 4.2 |
| 26 | Bis succinimide from alkenyl succinic anhydride and diethylene triamine | MoO$_3$ | Viscous Green Liquid | 2.6 |
| 27 | Salt of N-oleyl-1,3-propanediamine(Duomeen OL), with Di(2-ethylhexyl) dithiophosphoric acid | MoO$_3$ | Brown Liquid | 6.3 |

Test for Oxidation Induction Time by Pressure Differential Scanning Calorimetry (PDSC)

The Pressure Differential Scanning Calorimetry (PDSC) test method is a thin film high temperature catalytic oxidation test, for determination of oxidation induction time (OIT). The procedure used for this analysis was ASTM 6186-03. In the test, the compounds to be evaluated for antioxidancy performance were added at the required treat rate to a sample of Chevron Group II ISOVG 46 base oil containing no other additive. This test sample (6-9 mg) was placed in the center of an aluminum DSC pan and inserted into a DuPont 910 High Pressure DSC, equipped with a pressure cell and interfaced to a TA Instruments 2000 thermal analysis controller. The pressure cell of the DSC was closed, purged with $O_2$, equilibrated at 70° C., and heated to 210° C. at a rate of 40° C./min. When the temperature had reached 209° C. the cell was pressurized with oxygen to a pressure of 500 psi and the cell held at 210° C. After a period of time the test sample underwent an exothermic oxidative reaction; this event and magnitude of the associated heat effects compared to the inert reference were monitored and recorded. The data obtained was analyzed using TA Instruments Universal Analysis program V4.1D. The oxidation induction time (OIT; time to auto-oxidation) is the time at which the baseline intersects with a line tangent to the curve of the exothermal heat flow versus time scan. The OIT is reported in minutes. The magnitude of the OIT is an indication of the effectiveness of the compounds or compound mixtures under test as antioxidants; the larger the OIT the greater the antioxidant effect.

| Sample | Oxidation induction time (minutes) |
|---|---|
| 0.5% amine tungstate of Ex. 1 | 0 |
| 0.5% NA-LUBE AO142(Octyl/butyldiphenyl amine) | 2.8 |
| 0.5% NA-LUBE AO142(Octyl/butyldiphenyl amine) + 900 ppm amine tungstate of Ex. 1 | 12.0 |

Clearly the amine tungstates of the current invention provided synergistic antioxidant activity, in combination with aminic antioxidants. Synergistic antioxidant effects of combining amine tungstate compounds of the current invention with an aminic antioxidant were noted with a larger OIT for these combinations.

Oxidative Stability by Rotating Pressure Vessell Oxidation Test (RPVOT)

Also thermo-oxidative stability of these synergistic mixtures in combination with Group II base oil at various concentrations were determined using the ASTM D 2272 Rotating Pressure Vessell Oxidation Test (RPVOT) method.

The RPVOT test utilizes an oxygen-pressure bomb to evaluate the oxidation stability of oils in the presence of water and a copper catalyst coil at 150° C. The test oil, water and a copper catalyst coil, contained in a covered glass container, were placed in a vessel equipped with a pressure gauge. The bomb was charged with oxygen to a pressure of 90 psi, placed in a constant temperature oil bath at 150° C., and rotated axially at 100 rpm at an angle of 30° from the horizontal. The time period required for the pressure to drop to 25 psi is the measure of the oxidation stability of the test sample: the longer the time, the better the oxidative stability of the material.

| Sample in Chevron ISO VG 46 base Oil | W(ppm) | RPVOT minutes |
|---|---|---|
| No additive | | 38 |
| 0.5% NA-LUBE ® AO142(Octyl/butyldiphenyl amine) | — | 313 |
| 0.5% NA-LUBE ® AO142(Octyl/butyldiphenyl amine) + amine tungstate of Ex. 10 | 142 | 1359 |
| 0.5% NA-LUBE ® AO142(Octyl/butyldiphenyl amine) + amine tungstate of Ex. 11 | 133 | 1274 |
| 0.5% NA-LUBE ® AO142(Octyl/butyldiphenyl amine) + amine tungstate of Ex. 16 | 139 | 918 |
| 0.5% NA-LUBE ® AO142(Octyl/butyldiphenyl amine) + amine tungstate of Ex. 17 | 143 | 1202 |
| 0.5% NA-LUBE ® AO142(Octyl/butyldiphenyl amine) + amine tungstate of Ex. 15 | 145 | 1163 |
| 0.5% NA-LUBE ® AO142(Octyl/butyldiphenyl amine) + amine tungstate of Ex. 18 | 142 | 1170 |
| 0.5% NA-LUBE ® AO142(Octyl/butyldiphenyl amine) + amine tungstate of Ex. 8 | 142 | 828 |
| 0.5% NA-LUBE ® AO142(Octyl/butyldiphenyl amine) + amine tungstate of Ex. 9 | 142 | 532 |
| 0.5% NA-LUBE ® AO142(Octyl/butyldiphenyl amine) + amine tungstate of Ex. 5 | 142 | 801 |
| 0.5% NA-LUBE AO142(Octyl/butyldiphenyl amine) + amine tungstate of Ex. 12 | 140 | 1023 |
| 0.5% NA-LUBE AO142(Octyl/butyldiphenyl amine) + amine tungstate of Ex. 14 | 140 | 1790 |
| 0.5% NA-LUBE AO142(Octyl/butyldiphenyl amine) + amine tungstate of Ex. 13 | 140 | 636 |

Synergistic antioxidant effects of combining amine tungstate compounds of the current invention with an aminic antioxidant were once again noted with a larger induction time for these combinations.

| Sample in Chevron ISO VG 46 base Oil | W(ppm) | RPVOT minutes |
|---|---|---|
| No additive | | 38 |
| Amine tungstate of Ex. 1 | 144 | 32 |
| 0.5% NA-LUBE ® AO142(Octyl/butyldiphenyl amine) | — | 313 |
| 0.5% NA-LUBE ® AO142(Octyl/butyldiphenyl amine) + amine tungstate of Ex. 1 | 144 | 865 |
| 0.7% ZDDP(Zinc dialkyldithiophosphate) | — | 130 |
| 0.7% ZDDP(Zinc dialkyldithiophosphate) + amine tungstate of Ex. 1 | 144 | 488 |

Synergistic antioxidant effects of combining amine tungstate compounds of the current invention with an aminic antioxidant, and a dialkyl dithiophosphate were once again noted with a larger induction time for these combinations.

Friction Performance

The friction coefficients of compounds of current invention were evaluated in prototype motor oil using a modified ASTM D5707 SRV Ball on Plate protocol; 400N, 50 Hz; 1.00 mm stroke 120° C.; 120 min. The data showed an improvement in friction coefficient for compounds of current invention compared to the base oil with no friction modifier additive.

| Sample in Chevron ISO VG 46 base Oil, containing ashless dithiophosphate, ZDDP, triphenylphosphate ester, and alkylated naphthalene sulfonate rust inhibitor | W(ppm) | Final friction coefficient) after 120 min.) |
|---|---|---|
| No additive | — | 0.103 |
| Ex. 8 | 142 | 0.069 |
| Ex. 5 | 142 | 0.065 |
| Ex. 9 | 142 | 0.085 |
| Ex. 1 | 144 | 0.061 |
| Ex. 2 | 142 | 0.062 |
| Ex. 10 | 142 | 0.076 |
| Ex. 18 | 142 | 0.070 |
| Ex. 11 | 142 | 0.079 |
| Ex. 12 | 142 | 0.079 |
| Ex. 13 | 451 | 0.071 |
| Ex. 14 | 448 | 0.078 |
| Ex. 17 | 143 | 0.080 |
| Ex. 19 | 500 | 0.061 |

| Sample in Exxon Superflo 10w-30 oil | Mo(ppm) | Final friction coefficient) after 120 min.) |
|---|---|---|
| No additive | — | 0.135 |
| Molyvan 855 | 800 | 0.054 |
| Ex. 23 | 537 | 0.053 |
| Ex. 24 | 520 | 0.057 |
| Ex. 25 | 521 | 0.063 |
| Ex. 26 | 520 | 0.054 |

What is claimed is:

1. A lubricating oil composition comprising
a lubricating oil in an amount greater than 50% by weight;
an oil-soluble secondary diaryl amine, and/or an oil-soluble alkylated phenothiazine; and
at least one oil-soluble organo amine tungstate,
wherein the at least one organoamine tungstate is prepared by any of the following reactions
1) the reaction of a salt of N-oleyl-1,3-propanediamine with dinonyl naphthalene sulfonic acid and ammonium orthotungstate;
2) the reaction of a salt of N-oleyl-1,3-propanediamine with dinonyl naphthalene sulfonic acid and ammonium paratungstate;
3) the reaction of a salt of N-oleyl-1,3-propanediamine with dinonyl naphthalene sulfonic acid and tungstic acid hydrate derived from the reaction of sodium tungstate dihydrate with acid;
4) the reaction of a salt of N-oleyl-1,3-propanediamine with didodecyl naphthalene sulfonic acid and ammonium paratungstate;
5) the reaction of a salt of N-oleyl-1,3-propanediamine with didodecyl naphthalene sulfonic acid and ammonium orthotungstate;
6) the reaction of a salt of N-oleyl-1,3-propanediamine with didodecyl naphthalene sulfonic acid and tungstic acid hydrate derived from the reaction of sodium tungstate dihydrate with acid;
7) the reaction of a salt of N-oleyl-1,3-propanediamine with naphthenic acid and ammonium paratungstate;
8) the reaction of a salt of N-oleyl-1,3-propanediamine with naphthenic acid and ammonium orthotungstate;
9) the reaction of a salt of N-oleyl-1,3-propanediamine with naphthenic acid and tungstic acid hydrate derived from the reaction of sodium tungstate dihydrate with acid;
10) the reaction of N-oleyl-1,3-propanediamine with canola oil and ammonium paratungstate;
11) the reaction of N-oleyl-1,3-propanediamine with canola oil and ammonium orthotungstate;
12) the reaction of N-oleyl-1,3-propanediamine with canola oil and tungstic acid hydrate derived from the reaction of sodium tungstate dihydrate with acid;
13) the reaction of aminoethyl imidazoline with didodecyl naphthalene sulfonic acid and ammonium paratungstate;
14) the reaction of aminoethyl imidazoline with didodecyl naphthalene sulfonic acid and ammonium ortho tungstate;
15) the reaction of aminoethyl imidazoline with didodecyl naphthalene sulfonic acid and tungstic acid hydrate derived from the reaction of sodium tungstate dihydrate with acid;
16) the reaction of a salt of N-oleyl-1,3-propanediamine with di(2-ethylhexyl) phosphate and ammonium orthotungstate;
17) the reaction of a salt of N-oleyl-1,3-propanediamine with di(2-ethylhexyl) phosphate and ammonium paratungstate;
18) the reaction of a salt of N-oleyl-1,3-propanediamine with di(2-ethylhexyl) phosphate and tungstic acid hydrate derived from the reaction of sodium tungstate dihydrate with acid;
19) the reaction of a salt of N-oleyl-1,3-propanediamine with di(2-ethylhexyl)dithio phosphate and ammonium orthotungstate;
20) the reaction of a salt of N-oleyl-1,3-propanediamine with di(2-ethylhexyl)dithio phosphate and ammonium orthotungstate; and
21) the reaction of a salt of salt of N-oleyl-1,3-propanediamine with di(2-ethylhexyl) dithio phosphate and tungstic acid hydrate derived from the reaction of sodium tungstate dihydrate with acid;
22) the reaction of a salt of N-oleyl-1,3-propanediamine with di(oleyl) phosphate and ammonium orthotungstate;
23) the reaction of a salt of N-oleyl-1,3-propanediamine with di(oleyl) phosphate and ammonium paratungstate;
24) the reaction of a salt of N-oleyl-1,3-propanediamine with di(oleyl) phosphate and tungstic acid hydrate derived from the reaction of sodium tungstate dihydrate with acid.

2. A lubricating oil composition comprising
a lubricating oil in an amount greater than 50% by weight;
an oil-soluble secondary diaryl amine, and/or an oil-soluble alkylated phenothiazine; and
at least one oil-soluble organo amine tungstate,
wherein the at least one organoamine tungstate is derived from an amine prepared by any of the following reactions:
1. the reaction of N-oleyl-1,3-propanediamine with dinonyl naphthalene sulfonic acid;
2. the reaction of N-oleyl-1,3-propanediamine with didodecyl naphthalene sulfonic acid;
3. the reaction of N-oleyl-1,3-propanediamine with naphthenic acid;
4. the reaction of canola oil with N-oleyl-1,3-propanediamine;
5. the reaction of aminoethyl imidazoline with didodecyl naphthalene sulfonic acid;
6. the reaction of bis(2-hydroxyethyl) cocoamine and an alkyl ($C_{14}$-$C_{18}$) bis(2-hydroxyethyl) amine;
7. the reaction of N-oleyl-1,3-propanediamine with di(2-ethylhexyl) phosphonic acid;
8. the reaction of N-oleyl-1,3-propanediamine with di(oleyl) phosphonic acid; and
9. the reaction of N-oleyl-1,3-propanediamine with di(2-ethylhexyl) dithiophosphoric acid.

3. An oil-soluble organo amine tungstate prepared by a reaction selected from the group consisting of:
1. the reaction of a salt of N-oleyl-1,3-propanediamine with dinonyl naphthalene sulfonic acid and ammonium orthotungstate;
2. the reaction of a salt of N-oleyl-1,3-propanediamine with dinonyl naphthalene sulfonic acid and ammonium paratungstate;
3. the reaction of a salt of N-oleyl-1,3-propanediamine with dinonyl naphthalene sulfonic acid and tungstic acid hydrate derived from the reaction of sodium tungstate dihydrate with acid;
4. the reaction of a salt of N-oleyl-1,3-propanediamine with didodecyl naphthalene sulfonic acid and ammonium paratungstate;
5. the reaction of a salt of N-oleyl-1,3-propanediamine with didodecyl naphthalene sulfonic acid and ammonium orthotungstate;
6. the reaction of a salt of N-oleyl-1,3-propanediamine with didodecyl naphthalene sulfonic acid and tungstic acid hydrate derived from the reaction of sodium tungstate dihydrate with acid;
7. the reaction of a salt of N-oleyl-1,3-propanediamine with naphthenic acid and ammonium paratungstate;
8. the reaction of a salt of N-oleyl-1,3-propanediamine with naphthenic acid and ammonium orthotungstate;
9. the reaction of a salt of N-oleyl-1,3-propanediamine with naphthenic acid and tungstic acid hydrate derived from the reaction of sodium tungstate dihydrate with acid;
10. the reaction of N-oleyl-1,3-propanediamine with canola oil and ammonium paratungstate;
11. the reaction of N-oleyl-1,3-propanediamine with canola oil and ammonium orthotungstate;
12. the reaction of N-oleyl-1,3-propanediamine with canola oil and tungstic acid hydrate derived from the reaction of sodium tungstate dihydrate with acid;
13. the reaction of aminoethyl imidazoline with didodecyl naphthalene sulfonic acid and ammonium paratungstate;
14. the reaction of aminoethyl imidazoline with didodecyl naphthalene sulfonic acid and ammonium ortho tungstate;
15. the reaction of aminoethyl imidazoline with didodecyl naphthalene sulfonic acid and tungstic acid hydrate derived from the reaction of sodium tungstate dihydrate with acid;
16. the reaction of a salt of N-oleyl-1,3-propanediamine with di(2-ethylhexyl) phosphate and ammonium orthotungstate;
17. the reaction of a salt of N-oleyl-1,3-propanediamine with di(2-ethylhexyl) phosphate and ammonium paratungstate;
18. the reaction of a salt of N-oleyl-1,3-propanediamine with di(2-ethylhexyl) phosphate and tungstic acid hydrate derived from the reaction of sodium tungstate dihydrate with acid;
19. the reaction of a salt of N-oleyl-1,3-propanediamine with di(2-ethylhexyl)dithio phosphate and ammonium orthotungstate;
20. the reaction of a salt of N-oleyl-1,3-propanediamine with di(2-ethylhexyl)dithio phosphate and ammonium orthotungstate;
21. the reaction of a salt of salt of N-oleyl-1,3-propanediamine with di(2-ethylhexyl) dithio phosphate and tungstic acid hydrate derived from the reaction of sodium tungstate dihydrate with acid;
22. the reaction of a salt of N-oleyl-1,3-propanediamine with di(oleyl) phosphate and ammonium orthotungstate;
23. the reaction of a salt of N-oleyl-1,3-propanediamine with di(oleyl) phosphate and ammonium paratungstate; and
24. the reaction of a salt of N-oleyl-1,3-propanediamine with di(oleyl) phosphate and tungstic acid hydrate derived from the reaction of sodium tungstate dihydrate with acid.

4. The lubricating oil composition of claim 1, wherein the oil-soluble secondary diaryl amine is an alkylated diphenyl amine.

5. The composition of claim 1, wherein the oil-soluble secondary diarylamine present in an amount from about 0.075 to 2.5% by weight of the lubricating composition.

6. The composition of claim 1, wherein the oil-soluble secondary diaryl amine is of the formula

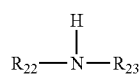

wherein $R_{22}$ and $R_{23}$ each independently represents a substituted or unsubstituted aryl group having from 6 to 30 carbon atoms.

7. The composition as described in claim 1, wherein the oil-soluble secondary diaryl amine is of the formula:

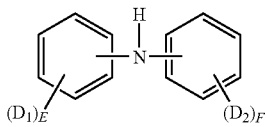

wherein D1 and D2 may be the same or different and each independently represents a hydrocarbyl radical of 1 to 28 carbon atoms. E and F may be the same or different and may equal 0, 1, 2 or 3.

8. The lubricating oil composition of claim 1, wherein the at least one organo amine tungstate is present in an amount sufficient to provide about 20 to 4000 ppm of tungsten in the lubricating composition.

9. The lubricating oil composition of claim 1, wherein the at least one organo amine tungstate is present in an amount sufficient to provide about 20 to 1000 ppm of tungsten in the lubricating composition.

10. The lubricating oil composition of claim 1, further comprising one or more antioxidant, wherein the antioxidant is a copper, molybdenum, nickel, or zinc naphthenate, oleate, stearate, dialkyldithiophosphate, dialkyldithiocarbamate, or mixtures thereof.

11. The lubricating oil composition of claim 1, further comprising at least one of the following additives: a dispersant, a detergent, a friction modifier, an antiwear additive, a corrosion inhibitor, a metal deactivator, a fuel economy agent, and a viscosity index improver.

12. The lubricating oil composition of claim 1, further comprising a phenolic antioxidant, a sulfur-containing antioxidant, a copper-containing antioxidant, a zinc-containing antioxidant, a nickel-containing antioxidant, a molybdenum-containing antioxidant, or mixtures thereof.

13. The lubricating oil composition of claim 1, further comprising a zinc dithiocarbamate, a nickel dithiocarbamate, a copper dithiocarbamate, a molybdenum dithiocarbamate, or mixtures thereof.

14. The lubricating oil composition of claim 1, further comprising one or more friction modifier comprising a glycerol monoester of a fatty acid, a glycerol diester of a fatty acid, a succinimide, a substituted succinimide, a glycolated succinimide, a borated succinimide, a fatty phosphite, a fatty acid amide, a fatty epoxide, a borated fatty epoxide, a borated glycerol ester, an alkoxylated fatty amine, a borated alkoxylated fatty amine, a metal salt of a fatty acids, a sulfurized olefin, a fatty imidazoline, a condensation product of a carboxylic acid and a polyalkylene-polyamine, a metal salt of an alkyl salicylate, an amine salt of an alkylphosphoric acid, or mixtures thereof.

15. The lubricating oil composition of claim 2, wherein the oil-soluble secondary diaryl amine is an alkylated diphenyl amine.

16. The composition of claim 2, wherein the oil-soluble secondary diarylamine present in an amount from about 0.075 to 2.5% by weight of the lubricating composition.

17. The composition of claim 2, wherein the oil-soluble secondary diaryl amine is of the formula

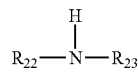

wherein $R_{22}$ and $R_{23}$ each independently represents a substituted or unsubstituted aryl group having from 6 to 30 carbon atoms.

18. The composition as described in claim 2, wherein the oil-soluble secondary diaryl amine is of the formula:

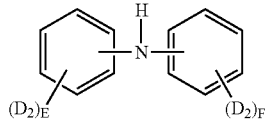

wherein D1 and D2 may be the same or different and each independently represents a hydrocarbyl radical of 1 to 28 carbon atoms. E and F may be the same or different and may equal 0, 1, 2 or 3.

19. The lubricating oil composition of claim 2, wherein the at least one organo amine tungstate is present in an amount sufficient to provide about 20 to 4000 ppm of tungsten in the lubricating composition.

20. The lubricating oil composition of claim 2, wherein the at least one organo amine tungstate is present in an amount sufficient to provide about 20 to 1000 ppm of tungsten in the lubricating composition.

21. The lubricating oil composition of claim 2, further comprising one or more antioxidant, wherein the antioxidant is a copper, molybdenum, nickel, or zinc naphthenate, oleate, stearate, dialkyldithiophosphate, dialkyldithiocarbamate, or mixtures thereof.

22. The lubricating oil composition of claim 2, further comprising at least one of the following additives: a dispersant, a detergent, a friction modifier, an antiwear additive, a corrosion inhibitor, a metal deactivator, a fuel economy agent, and a viscosity index improver.

23. The lubricating oil composition of claim 2, further comprising a phenolic antioxidant, a sulfur-containing antioxidant, a copper-containing antioxidant, a zinc-containing antioxidant, a nickel-containing antioxidant, a molybdenum-containing antioxidant, or mixtures thereof.

24. The lubricating oil composition of claim 2, further comprising a zinc dithiocarbamate, a nickel dithiocarbamate, a copper dithiocarbamate, a molybdenum dithiocarbamate, or mixtures thereof.

25. The lubricating oil composition of claim 2, further comprising one or more friction modifier comprising a glycerol monoester of a fatty acid, a glycerol diester of a fatty acid, a succinimide, a substituted succinimide, a glycolated succinimide, a borated succinimide, a fatty phosphite, a fatty acid amide, a fatty epoxide, a borated fatty epoxide, a borated glycerol ester, an alkoxylated fatty amine, a borated alkoxylated fatty amine, a metal salt of a fatty acids, a sulfurized olefin, a fatty imidazoline, a condensation product of a carboxylic acid and a polyalkylene-polyamine, a metal salt of an alkyl salicylate, an amine salt of an alkylphosphoric acid, or mixtures thereof.

* * * * *